US007682837B2

(12) United States Patent
Jain et al.

(10) Patent No.: US 7,682,837 B2
(45) Date of Patent: Mar. 23, 2010

(54) DEVICES AND METHODS TO FORM A RANDOMLY ORDERED ARRAY OF MAGNETIC BEADS AND USES THEREOF

(75) Inventors: Maneesh Jain, San Francisco, CA (US); Robert L. White, Stanford, CA (US); Lester A. Roberts, Palo Alto, CA (US)

(73) Assignee: Board of Trustees of Leland Stanford Junior University, Stanford, CA (US)

( * ) Notice: Subject to any disclaimer, the term of this patent is extended or adjusted under 35 U.S.C. 154(b) by 1853 days.

(21) Appl. No.: 09/923,752

(22) Filed: Aug. 7, 2001

(65) Prior Publication Data
US 2002/0081714 A1 Jun. 27, 2002

Related U.S. Application Data

(60) Provisional application No. 60/223,125, filed on Aug. 7, 2000, provisional application No. 60/202,357, filed on May 5, 2000.

(51) Int. Cl.
*G01N 33/551* (2006.01)
*C12Q 1/00* (2006.01)

(52) U.S. Cl. .............. 436/526; 436/518; 436/149; 436/150; 436/151; 435/4; 435/6; 435/7.1; 435/287.1; 435/287.2; 204/182.8; 204/299; 428/65.3; 428/694; 428/900; 428/141; 427/128; 427/129; 427/130; 427/131

(58) Field of Classification Search ........... 436/518, 436/526, 149–151; 435/4, 6, 7.1, 287.1, 435/287.2; 204/182.8, 299; 428/65.3, 694, 428/900, 141; 427/128, 129, 130, 131
See application file for complete search history.

(56) References Cited

U.S. PATENT DOCUMENTS 4,397,560 A * 8/1983 Andresen ............... 356/440

(Continued)

FOREIGN PATENT DOCUMENTS

WO 9639260 A1 12/1996

(Continued)

OTHER PUBLICATIONS

Barnes et al. (2000). "Recent developments in the encoding and deconvolution of combinatorial libraries," Curr Opin Chem Biol. 4(3):346-50.

(Continued)

*Primary Examiner*—Mark L Shibuya
*Assistant Examiner*—Pensee T Do
(74) *Attorney, Agent, or Firm*—Choate, Hall & Stewart LLP

(57) ABSTRACT

The invention includes devices and methods for forming random arrays of magnetic particles, arrays formed using these devices and methods, and to methods of using the arrays. The invention provides an assembly (chip) with magnetic domains that produce localized magnetic fields capable of immobilizing magnetic particles such as commercially available magnetic beads. Probe or sensor molecules can be coupled to the beads, which are then dispersed on the assembly, forming a random order array. The arrays can be used for analyzing samples, targets, and/or the interaction between samples and targets. The invention finds particular use in processes such as high-throughput genotyping and other nucleic acid hybridization-based assays.

67 Claims, 15 Drawing Sheets

U.S. PATENT DOCUMENTS

| | | | |
|---|---|---|---|
| 5,178,757 A * | 1/1993 | Corney | 210/222 |
| 5,270,163 A | 12/1993 | Gold et al. | |
| 5,395,498 A * | 3/1995 | Gombinsky et al. | 204/464 |
| 5,475,096 A | 12/1995 | Gold et al. | |
| 5,567,588 A | 10/1996 | Gold et al. | |
| 5,595,877 A | 1/1997 | Gold et al. | |
| 5,603,351 A | 2/1997 | Cherukuri et al. | |
| 5,637,459 A | 6/1997 | Burke et al. | |
| 5,683,867 A | 11/1997 | Biesecker et al. | |
| 5,705,337 A | 1/1998 | Gold et al. | |
| 5,747,169 A | 5/1998 | Fan et al. | |
| 5,965,452 A | 10/1999 | Kovacs | |
| 5,981,297 A | 11/1999 | Baselt | |
| 6,040,138 A | 3/2000 | Lockhart et al. | |
| 6,355,491 B1 * | 3/2002 | Zhou et al. | 436/518 |
| 6,432,630 B1 * | 8/2002 | Blankenstein | 435/4 |
| 6,440,520 B1 * | 8/2002 | Baglin et al. | 428/65.3 |

FOREIGN PATENT DOCUMENTS

| | | |
|---|---|---|
| WO | 9716561 A1 | 5/1997 |
| WO | 9853093 A1 | 11/1998 |
| WO | 9967641 A2 | 12/1999 |
| WO | 0048000 A1 | 8/2000 |
| WO | 0061720 A2 | 10/2000 |
| WO | 0063437 A2 | 10/2000 |
| WO | 0071243 A1 | 11/2000 |
| WO | 0071995 A2 | 11/2000 |
| WO | 0075373 A2 | 12/2000 |

OTHER PUBLICATIONS

Brenner et al. (2000). "Gene expression analysis by massively parallel signature sequencing (MPSS) on microbead arrays," Nat Biotechnol. 18(6):630-4.

Brown, P. and Botstein, D., (2000). "Exploring the new world of the genome with DNA microarrays," Nat. Genet. 21 (1 Suppl):33-37.

Czarnik. (1997). "Encoding methods for combinatorial chemistry," Curr Opin Chem Biol. 1(1):60-6.

Dickinson et al. (1996). "A Chemical-Detecting System Based on a Cross-Reactive Optical Sensor Array," Nature. 382, 697-700.

Dickinson et al. (1997). "Generating Sensor diversity Through Combinatorial Polymer Synthesis," Analytical Chemistry. 69:3413-18.

Dickinson et al. (1998). "Current Trends in 'Artificial Nose' Technology," Trends in Biotechnology. 16:250-58.

Dickinson et al. (1999). Self-Encoded Bead Sensor Arrays in the Design of an Artificial Nose, Analytical Chemistry. 71:2192-98.

Edelstein et al. (2000). "The BARC biosensor applied to the detection of biological warfare agents," Biosensors and Bioelectronics. 14:805-813.

Fan et al. (2000). "Parallel genotyping of human SNPs using generic high-density oligonucleotide tag arrays," Genome Res. 10(6):853-60.

Ferguson et al. (2000). "High-Denstiy Fiber-Optic DNA Random Microsphere Array," Analytical Chemistry. 72, 5218.

Haab et al. (2001). "Protein microarrays for highly parallel detection and quantitation of specific proteins and antibodies in complex solutions," Genome Biol. 2(2):research0004.1-0004.13.

Han et al. (2001). "Quantum-dot-tagged microbeads for multiplexed optical coding of biomolecules", Nat. Biotechnol. 19:631-635.

Hirschhorn et al. (2000). "SBE-TAGS: An array-based method for efficient single-nucleotide polymorphism genotyping," Proc. Natl. Acad. Sci. 97(22):12164-12169.

Lockhart, D. and Winzeler, E. (2000). "Genomics, gene expression and DNA arrays", Nature. 405(6788):827-826.

Maclean et al. (1997). "Encoded combinatorial chemistry: synthesis and screening of a library of highly functionalized pyrrolidines" Proc Natl Aced Sci U S A., 94(7):2805-10.

Michael et al. (1998). "Randomly Ordered Addressable High-Density Optical Sensor Arrays" Analytical Chemistry. 70:1242-48.

Ronaghi et al. "A Sequencing Method Based on Real-Time Pyrophosphate," Science. 281:363 (1998).

Steemers et al. (2000). "Screening unlabeled DNA targets with randomly ordered fiber-optic gene arrays," Nat Biotechnology. 18:91-94.

Walt. (2000). "Techview: Molecular Biology. Bead-Based Fiber-Optic Arrays," Science. 287:451-52.

White et al. (1996). "Rapid Analyte Recognition in a Device Based on Optical Sensor and the Olfactory System," Anlytical Chemistry. 68:2191-2202.

Ye et al. (2001). "Fluorescent microsphere-based readout technology for multiplexed human single nucleotide polymorphism analysis and bacterial identification,"Human Mutat. 17(4):305-16.

* cited by examiner

DEVICES AND METHODS TO FORM A RANDOMLY ORDERED ARRAY OF MAGNETIC BEADS AND USES THEREOF

CROSS REFERENCE TO RELATED APPLICATIONS

This application claims the benefit of U.S. Provisional Application No. 60/223,125, filed Aug. 7, 2000, which is incorporated herein by reference in its entirety for all purposes. Inventors' U.S. Provisional Application No. 60/202,357, filed May 5, 2000, is also incorporated herein by reference in its entirety.

This invention was made with U.S. Government support pursuant to grant no. HG 00205 from the National Institutes of Health. The U.S. Government may have certain rights in this invention.

FIELD OF THE INVENTION

Embodiments of the invention relate to devices and methods for forming arrays of magnetic particles, arrays of such particles, and uses of the arrays.

BACKGROUND OF THE INVENTION

Progress in biology and in chemistry is leading to an ever-increasing demand for high-throughput, cost-effective analysis of complex mixtures. This demand has in turn stimulated the development of compact, high-density array devices. These devices are used to perform a wide variety of assays in a number of different contexts. Such assays typically involve classes of molecules including nucleic acids, proteins, antibodies, small organic molecules, etc. Applications include genotyping, immunodiagnostics, and screening of drug candidates. For example, the complete DNA sequence of a number of organisms including humans has been determined or will be determined in the near future. The next step is to quantify and understand the DNA sequence variation within particular individuals, thereby enabling identification and possibly treatment of genetic diseases, personalized selection of medications based on an individual's genetic makeup (pharmacogenomics), and a deeper understanding of the genetic basis for phenotypic variability. Arrays will play a key role in developing the massively parallel technologies needed to realize these possibilities.

Although diverse in terms of the specific molecules and assays involved, a common conceptual scheme underlies most array technologies. In general, a probe or sensor molecule is attached in some fashion to a substrate. The probe is contacted with a sample (typically, though not necessarily, a complex mixture) and an interaction takes place between the probe or sensor and a component of the sample (a target), which is then detected. In many array-based assays the target is bound (either covalently or noncovalently) to the probe, and binding is detected via a range of different approaches, thereby revealing the presence, identity, or other features of the target.

In most array technologies, the identity of a probe is positionally encoded, i.e., the probe is attached either directly or indirectly to a typically planar surface, and the position of the probe on the surface serves to encode the identity of the probe. For example, oligonucleotide arrays are used to understand the DNA sequence variation between individuals, e.g., by performing single nucleotide polymorphism (SNP) genotyping. DNA obtained from an individual can be labeled (possibly after or during an amplification step) and then contacted with an array consisting of thousands of oligonucleotides attached to a substrate. Each of the oligonucleotides has a known sequence and is present at a known location on the substrate. The location of the hybridized nucleic acid molecule can be determined, e.g., by observing a fluorescent signal coming from the label. This location can be used to determine the sequence of the oligonucleotide bound to the DNA, which in turn reveals the sequence of the DNA. Similar approaches are widely used for determining MRNA expression patterns, and applications involving detection of proteins are contemplated. The current and potential future impact of DNA biochips is reviewed in Brown, P. and Botstein, D., "Exploring the new world of the genome with DNA microarrays", *Nat. Genet.*, 21 (1 Suppl):33-37, 2000 and in Lockhart, D. and Winzeler, E., "Genomics, gene expression and DNA arrays", *Nature*, 405(6788):827-826, 2000.

Arrays such as substrate-bound oligonucleotide arrays have been fabricated using ink-jet printing and high-speed robotics, which individually deposit the oligonucleotides on a substrate as spots. The oligonucleotides are then permanently bound to the substrate. Oligonucleotide arrays have also been fabricated using photolithography and light-directed combinatorial chemical synthesis. Other array manufacturing techniques include screen printing and photodeposition. These techniques typically require multiple fabrication steps, are labor-intensive and time-consuming, and are subject to variability. In addition, the identity of each probe on the array must generally be "pre-registered" by its position on the array. Such arrays are not easily adaptable or reusable as the probes are permanently bound to the substrate. In addition, these arrays suffer from a significant lack of flexibility since a new fabrication protocol is needed to change any of the probe sequences or to add new probes to the array.

Thus while array designs and manufacturing techniques such as those described above have already proven to be highly effective tools for genetic analysis and diagnostic applications, there is considerable room for improvement. The present invention addresses some of the limitations of currently existing array technologies.

SUMMARY OF THE INVENTION

Embodiments of the invention are directed to devices and methods for forming random arrays of magnetic particles, to arrays formed using these devices and methods, and to methods of using the arrays. As described further below, the invention provides an assembly comprising magnetic domains that produce localized magnetic fields capable of immobilizing magnetic particles such as commercially available magnetic beads. Probe or sensor molecules can be coupled to the beads, which are then dispersed on the assembly, forming a random order array. The arrays can be used for analyzing samples, targets, and/or the interaction between samples and targets. The invention finds particular use in processes such as high-throughput genotyping and other nucleic acid hybridization based assays. The invention offers a number of significant advantages in comparison with traditional DNA arrays in which probes are bound to a substrate.

In one aspect, the invention provides a device for forming an array of magnetic particles, the device comprising a substrate comprising a plurality of magnetic regions, wherein the magnetic regions produce a plurality of localized magnetic fields when magnetized, and wherein the localized magnetic fields are sufficient to trap a magnetic particle with a trapping energy at least five times greater than the thermal energy of the particle at room temperature. In certain embodiments of the invention the magnetic regions comprise a magnetic material, e.g., a ferromagnetic material such as cobalt. In certain embodiments of the invention the magnetic regions are rectangular and uniform in size and shape, and are arranged in a regular pattern on the substrate. The invention also provides a device for forming an array of magnetic particles, the device comprising a substrate comprising a plurality of magnetic regions, wherein the localized magnetic regions produce a plurality of localized magnetic fields, and wherein the magnetic regions project above the surface of the substrate.

The invention further provides a device for forming an array of magnetic particles, the device comprising (i) a non-magnetic substrate, and (ii) a plurality of magnetic regions located on the substrate, wherein a localized magnetic field exists between adjacent magnetic material regions when magnetized. In addition, the invention provides a device for forming an array of magnetic particles, the device comprising a substrate comprising a plurality of magnetic regions, wherein the magnetic regions produce a plurality of localized magnetic fields when magnetized, and wherein the localized magnetic fields generate forces sufficient to trap a magnetic particle with a trapping energy at least five times greater than the thermal energy of the particle at room temperature. According to certain embodiments of the invention a random array of magnetic particles is formed using any of the above devices. Any of the devices of the invention may comprise one or more of (i) a flux circulator, (ii) integrated photodetectors, and (iii) a microfluidic assembly.

In another aspect, the invention provides a randomly ordered array of magnetic particles. In certain embodiments of the invention the magnetic particles are magnetic beads, e.g., superparamagnetic beads. The beads may be encoded in any of a variety of ways. According to certain embodiments of the invention a plurality of the beads comprise a detectable moiety such as a fluorescent molecule or a hybridization tag. According to certain embodiments of the invention a plurality of the beads comprise a probe, which may be used, for example, to analyze a sample, e.g., to detect the presence of a target in a sample.

In another aspect, the invention provides methods of forming an array of magnetic particles comprising contacting any of the devices of the invention with a plurality of magnetic particles. The invention further provides a method of forming an array of magnetic particles comprising contacting magnetic particles with a device comprising magnetic regions that produce localized magnetic fields, whereby a plurality of the magnetic particles are trapped by the localized magnetic fields. According to certain embodiments of the invention the magnetic particles are magnetic beads, e.g., superparamagnetic beads. The invention further provides an array of magnetic particles formed according to any of the preceding methods.

In another aspect, the invention provides methods of analyzing a sample. One such method comprises (i) contacting the sample with magnetic particles, wherein each of a plurality of the magnetic particles comprises a probe, (ii) forming an array of the magnetic particles, and (iii) determining whether a probe interacts with a target in the sample. Another such method comprises (i) contacting the sample with magnetic particles, wherein each of a plurality of the magnetic particles comprises a probe, (ii) forming an array of the magnetic particles, and (iii) performing a genotyping assay, a hybridization assay, an SBE assay, an OLA assay, an ASPE assay, an allelic PCR assay, an exonuclease assay, and an invasive cleavage assay. Another such method comprises (i) contacting the sample with magnetic particles, wherein each of a plurality of the magnetic particles comprises a probe, (ii) forming an array of the magnetic particles, and (iii) performing an ELISA assay. Various detection methods may be used to detect the beads, probes, and/or targets. Appropriate detection modalities include confocal array scanners and charge coupled devices. The methods may include a step of decoding the beads and/or probes. The methods may be used, for example, to detect the presence of a particular target in a sample and/or to determine the identity of a target in a sample.

In another aspect, the invention provides a method of fabricating a device comprising steps of (i) providing a substrate and (ii) producing magnetic regions in or on the substrate, wherein the magnetic regions produce a plurality of magnetic fields when magnetized, and wherein the localized magnetic fields are sufficient to trap a magnetic particle with a trapping energy at least five times greater than the thermal energy of the particle at room temperature. Additional fabrication methods are also provided.

These and other embodiments of the invention and methods of use thereof are further described below.

This application refers to various patents, publications, scientific articles, books, and documents available on World Wide Web sites on or before Aug. 7, 2001. The contents of all of these items are hereby incorporated by reference in their entirety.

DEFINITIONS

Figure 1:
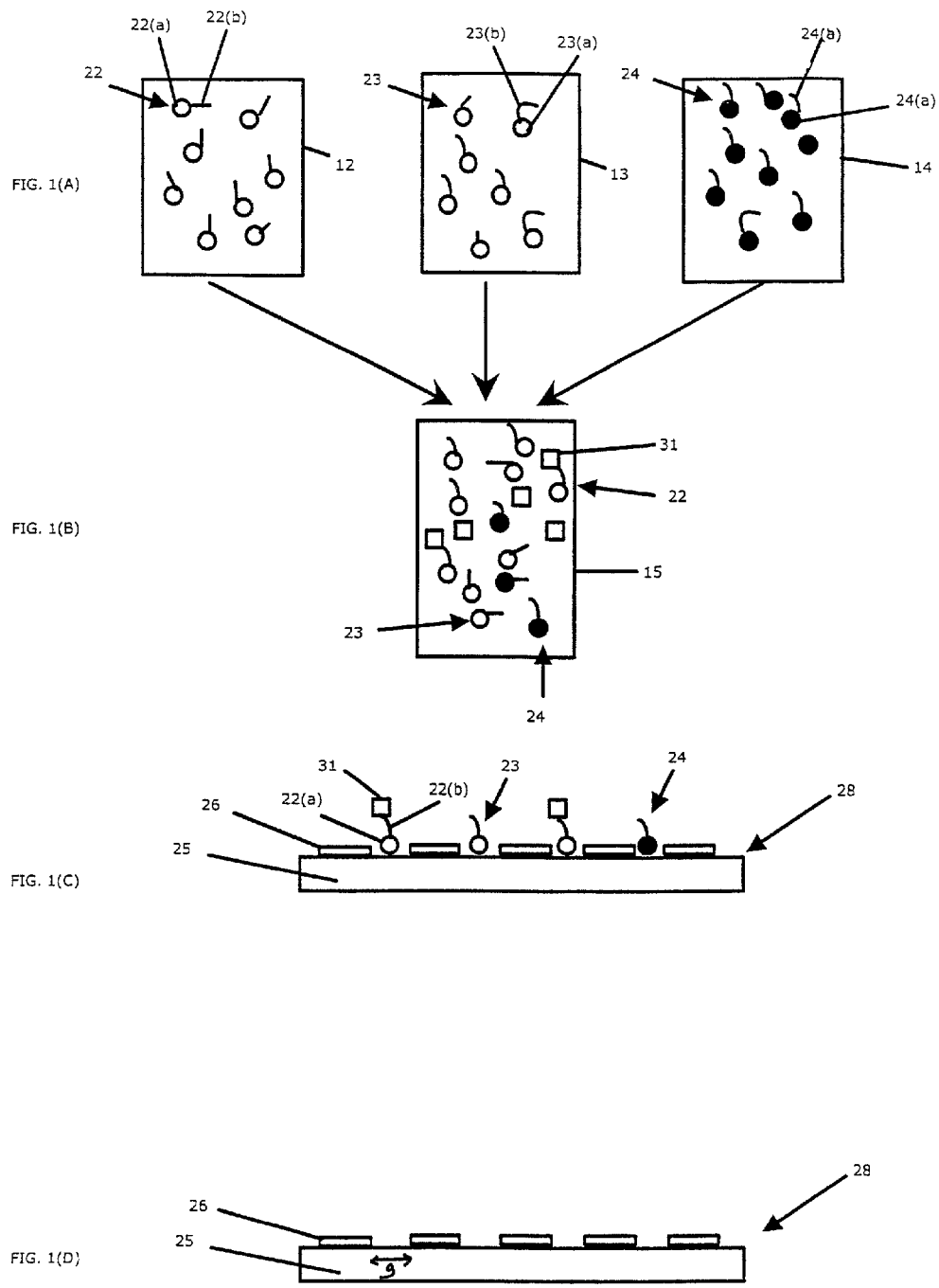
FIGS. 1(A) to 1(D) are side and cross-sectional views illustrating use of the magnetic chip of the invention in a hybridization assay.

Array: As used herein, an array refers to any arrangement of elements (array elements) in physical space. In general, the elements are arranged on a substrate though this need not be the case. For example, an array of magnetic beads may be suspended in space by magnetic forces. The elements can be, for example, beads; probes; molecules; domains having different biological, chemical or physical properties (including magnetic or electric properties) to those of the substrate, etc. The elements need not be physical elements but can be, for example, locations at which attachment or immobilization (either reversible or irreversible) of such entities can occur. Thus one can speak of an array of beads, an array of probes, an array of magnetic regions, an array of gap regions, an array of sites or locations (e.g., attachment sites), an array of arrays, etc. The term "array" is also used to refer to the substrate or mechanism that provides locations for array elements. For example, a substrate on which beads are dispersed or above which they are suspended, or a substrate to which oligonucleotides are bound may be referred to as an array.

The elements in an array need not be identical, although frequently this is the case. The elements may have some similar or identical properties (e.g., they may all be magnetic beads, oligonucleotides, etc.) while they may differ in terms of other properties (for example, beads may contain different dyes for encoding purposes, may be linked to different probes, etc.) An array may have a regular pattern of elements (e.g., a grid-like arrangement consisting of mutually perpendicular rows and columns of elements), though this need not be the case. A "pattern" in this sense refers to an arrangement that has a repeating unit cell. However, the array elements in an array may also be randomly positioned. In the context of the present invention, an embodiment described below comprises an array with a regular pattern of magnetic regions and attachment sites for beads. However, the array of beads that ultimately results is random in at least two senses. First, not all attachment locations necessarily contain a bead, while some attachment locations may contain multiple beads. Second, different populations of beads may be used to form a single array, and the identity of a bead at any particular attachment location is random in the sense that it is not predictable in advance (although the relative proportion of beads from different populations may provide a statistical basis for predicting the likelihood that a bead at any given location is from a particular bead population).

An array may be characterized in terms of its density (i.e., the average number of elements present per unit area). For example, an array having a density of approximately 10,000,000 or greater elements per $cm^2$ may be characterized as a very high density array. An array having a density of approximately 50,000 to 10,000,000 elements per $cm^2$ may be characterized as a high density array. However, these terms are relative and flexible, and their meaning is likely to change over time as higher and higher density arrays become available.

Array element: An array element, also referred to as an array feature, is any entity that may be present in the form of an array. Array elements can be, for example, beads; probes; molecules; domains having different biological, chemical or physical properties (including magnetic or electric properties) to those of the substrate, etc. The elements need not be physical elements but can be, for example, locations at which attachment or immobilization (either reversible or irreversible) of such entities can occur. Thus one can speak of an array of beads, an array of probes, an array of magnetic regions, an array of gap regions, an array of sites or locations (e.g., attachment sites), an array of arrays, etc. An array element may itself contain subelements. For example, a bead array element may have multiple molecules (e.g., probes) bound to it. An oligonucleotide array may consist of an array of spots, each spot containing multiple individual oligonucleotides.

Attachment location or site: As used herein, an attachment location or site is a location in 3-dimensional space at which an array element may be present. For example, in the context of a magnetic chip of the invention, an attachment location is a site at which a localized magnetic field exists or can be generated, sufficient to cause a magnetic bead to become immobilized (trapped) with a trapping energy greater than the thermal energy of the bead.

Biocompatible: As used herein, the term biocompatible refers to a material that will not cause, catalyze, or otherwise contribute to an appreciable chemical or physical reaction that will alter the structure of a biomolecule such as a nucleic acid, protein, carbohydrate, or lipid or an intact cell or subcellular fraction, under experimental conditions and over a time scale typical of standard biological or chemical assays for interaction between molecules. In particular, the material should not damage, inhibit, or otherwise interfere with nucleic acid hybridization of with the activity enzymes typically used for molecular biology procedures such as amplification, ligation, nucleotide polymerization, etc.

Complementary: As is well known in the art, with reference to nucleic acid molecules, complementary nucleic acid molecules are able to hybridize with each other via base pairing (e.g., hydrogen bonding between A and G, between C and T, etc.). The degree and specificity of hybridization is affected by the stringency of the conditions under which the nucleic acid molecules are exposed to each other. Factors such as temperature, ionic strength of the solution, pH, presence of destabilizing agents such as formamide or stabilizing agents may all influence the degree and specificity of hybridization. Hybridization conditions are generally referred to as high, medium, or low stringency, although the meanings assigned to these terms are variable and the effect of hybridization conditions is also sequence-specific. One of ordinary skill in the art will be able to select appropriate hybridization conditions or systematically vary such conditions to perform the various assays described herein. In general, stringent conditions are selected to be approximately 5-10° C. lower than the thermal melting point ($T_m$) for the specific double-stranded sequence at a particular pH and ionic strength, where the $T_m$ is the temperature at which 50% of the probes complementary to the target hybridize to the target at equilibrium, assuming targets are present in excess. Typical pH and salt concentrations for stringent conditions are approximately 0.01 to 1.0 M at pH 7.0. Information about hybridization of nucleic acids is found in Tijssen, *Techniques in Biochemistry* and *Molecular Biology—Hybridization With Nucleic Acid Probes*, Parts I and II, Elsevier Science, Ltd., 1993; Maniatis, T., Sambrook, J. and Fritsch, E., *Molecular Cloning: A Laboratory Manual* (3 Volume Set), Cold Spring Harbor Laboratory Press, Cold Spring Harbor, 1989 and its successor; and in Ausubel, et al., Current Protocols in Molecular Biology, John Wiley & Sons, New York, 2000.

In general, a nucleic acid probe for detecting a nucleic acid target is complementary to the target. However, such complementarity need not be perfect. A certain number of base pair mismatches may still allow hybridization under the stringency conditions selected. Where the nucleic acids are sufficiently complementary to allow hybridization under the selected conditions, they may be referred to as substantially complementary. For certain assays that may be employed in the context of the present invention, probes are able to distinguish between targets that differ by a single nucleotide.

Localized magnetic field: As used herein, a localized magnetic field is a magnetic field that substantially exists in the volume between the north pole of a first magnetic region and the south pole of a second magnetic region or substantially exists in the volume between the north and south poles of a single magnetic region.

Magnetic: The term magnetic, as used herein, includes ferromagnetic, paramagnetic, and superparamagnetic materials. Note that a magnetic entity need not be formed entirely of a magnetic material but may instead comprise both magnetic and nonmagnetic materials, e.g., a "magnetic bead" may comprise a nonmagnetic material with portions of magnetic material dispersed therein.

Magnetic particle: The concept of magnetic particles is discussed more fully below. It is noted that a magnetic particle can refer to any entity that includes a sufficient amount of a material that possesses magnetic properties such that the entity itself possesses magnetic properties. Magnetic materials include ferromagnetic, paramagnetic, and superparamagnetic materials and materials including such materials. In general, the term particle implies that the dimensions of the particle are small relative to dimensions of typical visible objects in the human environment. In the context of the present invention particles generally have a largest dimension of less than approximately 200 µm. Particles may have a regular shape, e.g., a substantially spherical shape, though this need not be the case. Typical magnetic particles in the context of the present invention are substantially spherical and have a diameter ranging from nanometers (e.g., 5-20 nm) to microns (e.g., 1-20 microns). However, particles with dimensions falling outside these limits may also be used.

Magnetic region or domain: This term refers to any portion of a substrate that possesses or can be modified to possess magnetic properties, or to a structure that can be applied or added to a substrate, wherein the structure possesses or can be modified to possess magnetic properties. Where the structure projects from a substrate surface, i.e., where the structure exists in three dimensions with respect to a two-dimensional surface, the structure may be referred to as a magnetic island. In general, a magnetic region or domain will contain a magnetic or magnetizable material such as iron, cobalt, nickel, or certain ceramics. The substrate itself may also possess magnetic properties although, in general this is not the case for the particular embodiments of the invention described in detail herein. Note that a magnetic region may exist in a magnetized or demagnetized state.

Population: As used herein, a population refers to a group of entities that are similar with respect to some significant feature. For example, a population of beads may be similar in that beads in the population incorporate the same encoding moiety at the same amount or concentration. A population of beads may be similar in that the beads in the population have the same probe coupled thereto. Beads from different populations may be pooled to create a mixed population. Note that in a situation in which beads from different populations are coupled to different probes or incorporate different detectable moieties, not all beads in a particular population need be coupled to the probe or incorporate the moiety. For example, as is well known to one of ordinary skill in the art, coupling reactions are less than 100% efficient. It is sufficient that a significant number of beads in a first population exhibit the characteristic that defines that population while not exhibiting the characteristic(s) that define other populations with which the first population is to be mixed.

Probe or sensor: An entity that can indicate the presence and/or abundance of a molecule of interest (a target or analyte) or can indicate the occurrence of a chemical reaction or a molecular interaction of interest. The indication may include reversible or irreversible binding of the target to the probe, although this need not be the case. The probe may itself be detectable or may be modified to be detectable, though this need not be the case. In general, the purpose of a probe is to allow detection of the presence or abundance of a target molecule or to allow detection of the occurrence of a chemical reaction or molecular interaction. Therefore, the combined presence of probe and target, or the occurrence of the chemical reaction or molecular interaction in the presence of the probe should ultimately result in a detectable readout. Probes include nucleic acid molecules, proteins (including antibodies and enzymes), aptamers, modified nucleic acids, modified proteins, etc. For example, an appropriate probe for indication of the presence of a target single-stranded nucleic acid molecule having a particular sequence would be a substantially complementary single-stranded nucleic acid molecule able to hybridize with the target.

Sample: A sample is any material that may contain a molecule or molecule(s) of interest. For example, a sample obtained from a subject may include, but is not limited to, any or all of the following: a cell or cells, a portion of tissue, blood, serum, ascites, urine, saliva, and other body fluids, secretions, or excretions. The term "sample" also includes any material derived by processing such a sample. Derived samples may include cell extracts or lysates, nucleic acids or proteins extracted from the sample or obtained by subjecting the sample to techniques such as amplification or reverse transcription of mRNA, etc. A sample may comprise material obtained from the environment, e.g., air, water, soil, or derived by processing such a sample. A sample may comprise natural or synthetic compounds, including but not limited to products of bacterial metabolism, synthesized organic molecules such as combinatorial chemical libraries, etc.

Substrate: A substrate, or solid support, as used herein refers to any material that contains or provides, or can be modified to contain or provide, locations for array elements. In the context of the present invention, an appropriate substrate is generally a material that contains or can be modified to contain, magnetic material regions, either as part of the substrate or added to it. Generally the substrate is planar, though this need not be the case. Generally the substrate has sufficient strength and hardness to allow routine laboratory handling. Examples of substrates include, but are not limited to, silicon or silicon-based materials, glass and modified or functionalized glass, plastics and modified or functionalized plastics, (including acrylics, polystyrene, polypropylene, polyethylene, etc.), metals, and ceramics. The substrate can have or lack magnetic properties.

Target: A material or entity whose presence and/or abundance is to be detected or whose identity is to be determined by an assay. A target may interact either directly or indirectly with a probe. Such interaction may include reversible or irreversible binding or association. A target may be a nucleic acid molecule, a protein, carbohydrate, lipid, receptor ligand, antigen, a small organic molecule, etc. Without intending to be limiting, a target nucleic acid sequence may be, a gene, a portion of a gene, a regulatory sequence, DNA, RNA, mRNA, cDNA, etc. For example, a target may be a single-stranded nucleic acid molecule including a genomic region that has been found to contain a single nucleotide polymorphism. A target may be contained within a portion of a larger molecule, and multiple target domains may exist within a single molecule.

DETAILED DESCRIPTION

I. Overview

The present invention encompasses the realization that randomly ordered micoarrays offer significant advantages in terms of flexibility, simplicity of fabrication, statistical robustness, and high throughput. The invention provides a device containing magnetic regions or domains and methods of using the device to generate randomly ordered arrays of magnetic particles. The invention further provides arrays formed using the device and methods of using the arrays, e.g., for detection of molecules of interest. The device of the present invention may be referred to herein as a magnetic chip. In one embodiment, the invention employs magnetic beads, which are dispersed onto the surface of the chip, forming array elements. The magnetic domains generate localized magnetic fields that facilitate reversible yet robust attachment of the magnetic beads to the chip and constrain their location. According to the invention, probes are attached to individual beads, which are then distributed randomly on the chip, forming array elements. The beads are magnetically coupled to the chip. In certain embodiments of the invention the arraying can be performed simply by dispensing a bead solution onto the chip (e.g., using a pipette), or by employing a gentle fluid flow.

The locations at which a bead may attach to the chip are largely determined by the configuration and features of the magnetic domains and of the gap regions between the magnetic domains. Such features include, among others, the dimensions of the magnetic domains and gap regions, the structure of the magnetic domains, and the spatial relationships between the magnetic domains and gap regions. Thus the potential locations of the beads are in large part a function of the chip design. In certain embodiments of the invention the attachment locations form a grid-like pattern as in conventional oligonucleotide or cDNA microarrays, and the chip configuration is optimized such that a single bead is attached at each occupied attachment location. The distribution is random in the sense that a particular bead may attach to any attachment location. In certain embodiments of the invention the density of attachment locations is greater than 10,000 per mm$^2$, making the arrays suitable for high throughput applications and offering the potential for an "array of arrays" format on a single chip.

The sample can be contacted with the beads prior to their dispersal on the chip or after dispersal has occurred. For example, when the assay involves nucleic acid hybridization, beads with attached probes can be mixed with sample prior to dispersal, or hybridization can be performed after the beads are attached to the chip. The identity of the bead, and thus of the probe associated with that bead, can be encoded using any of a variety of approaches as described below. Interaction (e.g., binding) between the probe and a target can be detected and the identity of the bead determined by appropriate decoding. Alternately, the identity of the probe can be determined directly (e.g., by microsequencing in the case of a DNA probe).

FIG. 1 presents a conceptual outline of a typical assay (e.g., a hybridization-based assay) that may be performed according to the invention. FIG. 1(A) represents three populations 12, 13, and 14, of magnetic beads. Typically the beads in each population will have been labeled, e.g., with a fluorescent dye or hybridization tag, so that beads from a given population may later be distinguished from beads of a different population. However, this need not be the case. The beads will typically be in a fluid medium. Different probes 22(b), 23(b), and 24(b) are attached to beads 22(a), 23(a), and 24(a) forming bead-probe units 22, 23, and 24. Each probe is able to detect a particular target. For example, each probe may be a nucleic acid that is complementary to a particular target nucleic acid.

As shown in FIG. 1(B), beads from each of the populations are combined to form a mixture 15, to which a sample containing one or more target molecules 31 is added. Typically the target is labeled in some fashion so that it is detectable. The sample could also be added to the individual bead populations prior to mixing. The relative number of beads from different populations may be varied, e.g., depending upon the expected abundance of target, the sensitivity desired, etc. In general, any number of beads from the multiple populations can be used, depending upon the redundancy desired. The sample may contain a single type of target molecule or multiple different target molecules, and the abundance of the target molecule(s) may vary. The mixture is incubated for a period of time to allow interaction between probe(s) and target(s). For example, in a hybridization-based assay the mixture would be incubated to allow hybridization between complementary probes and targets.

Figure 2:
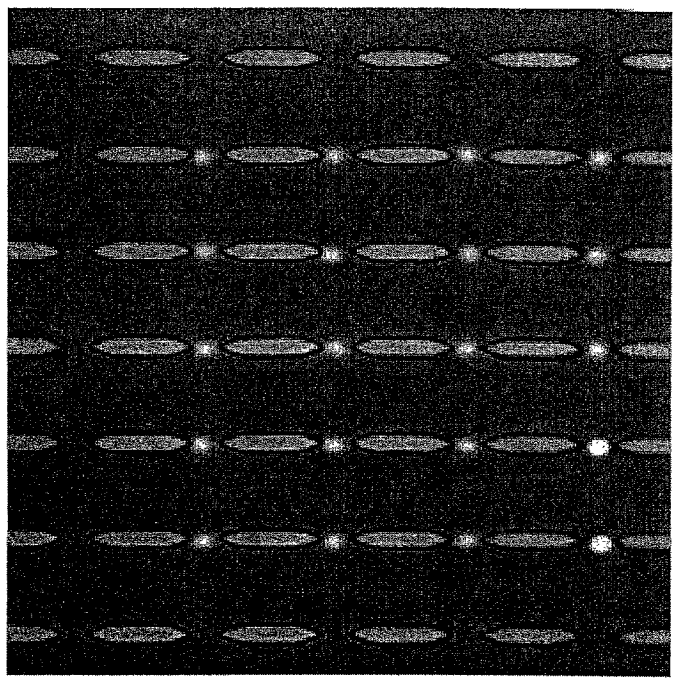
FIG. 2 shows a conceptual image of a magnetic chip containing diamond-shaped magnetic regions with arrayed beads.
Figure 2:
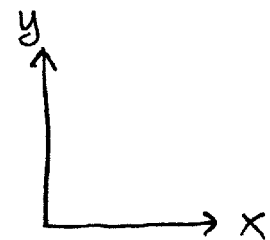

Following the incubation period the beads are introduced to the magnetic chip 28 by any convenient means, e.g., using a pipette or via a channel. As shown in FIG. 1(C), the magnetic chip includes magnetic regions 26 referred to as magnetic islands, positioned in a regular pattern on a substrate 25. The beads are immobilized by the localized magnetic field that exists between adjacent magnetic domains. Following a brief period (e.g., seconds to minutes) during which bead trapping takes place, excess bead solution containing unbound beads is removed. While the possible sites at which beads may be trapped are arranged in a regular pattern, the final arrangement of beads is random, as described further below. FIG. 2 shows a conceptual image of a magnetic chip containing diamond-shaped magnetic regions with arrayed beads. After formation of the array and removal of excess beads, the beads, probes, and/or targets may be detected according to any appropriate detection means, after which the beads can be removed, e.g., using a fast fluid flow. The chip may then be reused.

In general, the bead or its attached probe will have been labeled with some detectable moiety, and the target will have been labeled with a different detectable moiety. The labeling of the target allows detection of the interaction between probe and target, while the labeling of the bead or probe allows identification of the probe, which may further identify or indicate the presence of the particular target with which that probe interacts. Interactions may include binding (e.g., in the case of a hybridization-based assay) but may also include enzymatic reactions, etc. Interaction may result in quenching of a detectable marker, occurrence of an enzymatic reaction that may be detected, etc. As will be evident to one of ordinary skill in the art, numerous variations on the preceding scheme are possible, some of which are described in further detail below.

According to certain embodiments of the invention the chip is produced using variations of conventional semiconductor fabrication methods. Like other semiconductor fabrication methods, this is a readily scalable technology. The invention presents a number of other advantages over existing technologies for forming either positionally encoded or randomly ordered arrays. Among these are multiple reuse via a simple wash and/or demagnetization, simplicity and flexibility of chip design and fabrication, compatibility with on-chip electronics such as photodetection, and direct compatibility with bead-based nucleic acid/protein protocols. These include essentially any of the numerous assays for which substrate-bound oligonucleotide or cDNA arrays are currently employed.

In general, the use of bead-based approaches offers significant advantages over arrangements in which probe is bound to substrate. Once a substrate-bound array is prepared, changing or adding probes requires fabrication of a new array. In contrast, with bead-based approaches a new probe may be substituted or added by simply preparing a population of beads bearing that probe. The selection of probes is entirely flexible and can occur at the time of the assay rather. The degree of redundancy can be varied by varying the number of beads that bear any particular probe and/or by varying the ratio of beads bearing different probes. Thus the assay can be conveniently tailored as desired by the practitioner, depending on the particular application, instead of being constrained by a selection of probes that was made by a chip manufacturer.

The fact that assays involving interactions between molecules (e.g., hybridization between probe and target, enzymatic reactions, etc.) can be performed on the surface of a mobile bead in a tube rather than on an immobile surface provides further advantages. Rather than a situation in which only one of the molecules is freely diffusing in three dimensions, with bead-based approaches both interacting molecules can diffuse in three dimensions. This results in decreased time requirements and/or increased assay sensitivity. Multistep protocols that involve the sequential addition and/or removal of reagents may also be performed more conveniently using beads. Magnetic beads offer a particular advantage in this regard since their magnetic properties make it possible to readily isolate and/or wash the beads. In addition, the bead platform offers greatly increased potential for multiplexing and for redundancy to ensure statistical robustness even with random sampling.

While the foregoing advantages apply in general to bead-based assays, they may be of particular relevance for assays including hybridization steps, such as genotyping assays, including multiplex genotyping assays. These advantages may be summarized as follows, in the context of a comparison of bead-based and conventional DNA chip arrays (e.g., oligonucleotide arrays in which probe is bound to substrate such as those described in U.S. Ser. No. 6,040,138) for multiplex genotype assays:

(i) Reduced Hybridization Time

Tagged sample hybridization to beads in solution will reduce the hybridization time by one to several orders of magnitude. This reduction occurs because the effective concentration of an immobilized probe on the bead surface is much higher than that of a probe on a chip surface. Mobility and diffusion of both the probe and the target greatly enhance the hybridization efficiency.

(ii) Improved Sensitivity

Conversely, for the same hybridization time, the sensitivity of bead-based detection is better by orders of magnitude. Efficient hybridization using a bead-based approach has been shown over several hours using 100 fM target (or, 1 attomole of target in 10 µl) (Ferguson, et al., *Anal. Chem.*, 72:5618-5624, 2000). Over similar periods of time, inventors have shown that conventional DNA arrays (e.g., substrate-bound oligonucleotide arrays available from Affymetrix, Inc.) typically require approximately a 12-14 hour hybridization time using 10 pM target (or, 100 attomoles in 10 µl) for reasonable target detection. Hence, sensitivity is improved typically by two orders of magnitude. This has the advantage of reducing the level of sample amplification required, keeping it well in the linear regime. One can use less genomic template in the assay. Potentially, PCR steps could be eliminated in favor of other reduced amplification schemes.

(iii) Improved Signal to Noise Ratio

The total number of sites available for sample hybridization is similar when comparing one bead to one feature (i.e., one spot of probe) on a typical substrate-bound DNA array. However, randomly ordered bead arrays utilize built-in redundancy which allows 20-50 fold over-sampling, leading to much-improved signal to noise ratios and better accuracy in the data. A 20 µm$^2$ oligonucleotide (oligo) probe feature on a chip surface typically contains 200,000 full-length oligos (full-length probe densities on oligo synthesized arrays are typically ~500 oligos/µm$^2$). Functionalized beads (e.g., approximately 3 µm in diameter) can typically bind over 100,000 oligo probes.

(iv) Flexibility

Bead arrays can easily be configured to contain from ten to several thousand different probes in real time simply by using different batches of encoded beads. This provides a great deal of flexibility from experiment to experiment. The small size of the arrays (~10,000 features/mm$^2$) also lends itself to integration with microfluidics as described below. Finally, the redundancy levels can be adjusted to improve sensitivity or to pack more probes per run.

(v) Improved Selectivity

Washing protocols can be more uniform and effective on a solution of beads than performing washes by flowing buffers over a surface. Flow patterns and local washing stringency are typically very hard to keep uniform in the latter.

The invention represents an efficient, cost-effective, and flexible platform for genotyping assays, among others. Accurate genotyping of 10,000 or more samples can be performed in a single run. Since the arraying and detection processes take only on the order of 10 minutes per run, very high throughput is possible. Genotyping humans for common diseases and disorders and various polymorphisms of significance may require examining thousands of individuals for approximately 500,000 markers. Each run on a chip may examine one individual, however multiplexing schemes can be used to examine multiple different individuals for all these markers at the same time. Since all samples are interrogated simultaneously the cost per sample (not including PCR costs) and the time per run may be reduced by a factor of 100 or more as compared with using singleplex detection methods.

The following sections provide details of certain embodiments of the invention, from which these advantages will become more evident. As will be clear to one of ordinary skill in the art, a large number of variations may be made.

II. Chip Design and Manufacture

A. Design Considerations

FIG. 1(D) shows a schematic cross-sectional view of one embodiment of the invention. According to this embodiment the chip comprises a substantially flat, nonmagnetic substrate 25 with magnetic regions 26 projecting above the surface. In this embodiment of the invention the magnetic regions are referred to as magnetic islands, though this is not intended to limit the invention to magnetic regions that project above the substrate surface. The magnetic islands are arranged in a grid-like pattern, i.e., in mutually perpendicular rows and columns similar to those found in conventional oligonucleotide arrays. Such an arrangement may be convenient for bead detection and data processing using existing image processing tools and software. In addition, a regular arrangement allows for optimization of chip geometries in all regions. However, it will be appreciated that other configurations are possible and are within the scope of the invention.

As indicated in FIG. 1(D), the magnetic islands are separated by gap regions of sufficient length g to accommodate a bead.

Figure 3:
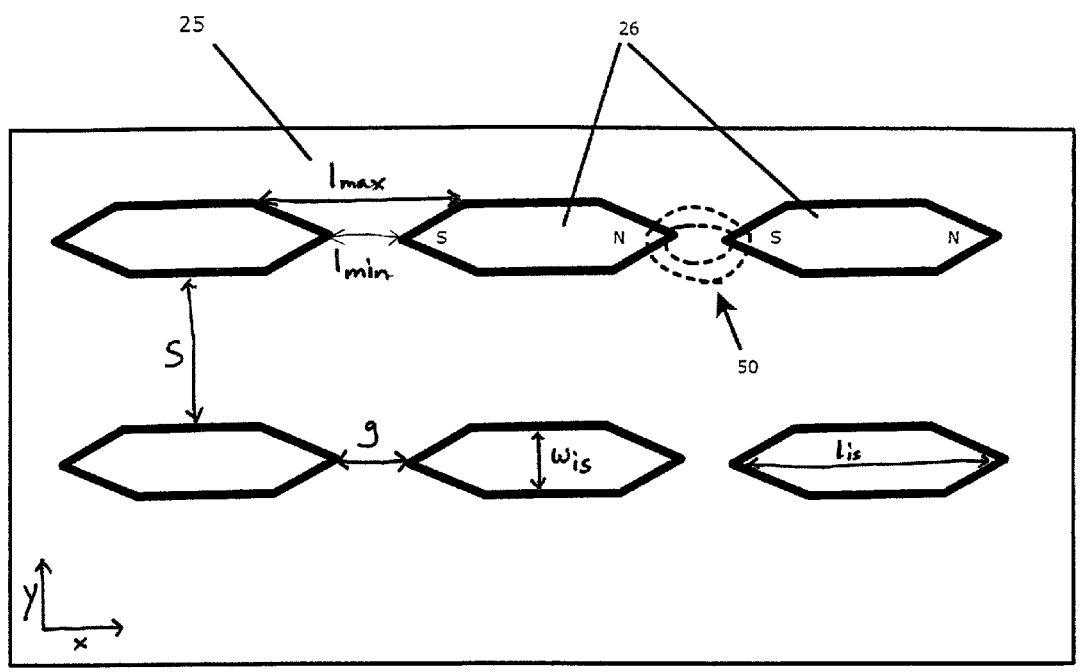
FIG. 3 is a schematic view of a portion of a magnetic chip.

FIG. 3 shows a schematic view looking down on a chip from above. For descriptive purposes x and y axes are depicted on the figure while the z dimension would point upwards perpendicularly from the page. The north and south poles are indicated on the diamond-shaped magnetic islands, and the localized magnetic field 50 within a gap region is also indicated. The distance g between the ends of the magnetic islands is sufficient to accommodate a bead. In certain embodiments of the invention the localized field traps (immobilizes) a single bead in the gap region between the magnetic islands.

In this embodiment the chip design involves selection of a number of parameters including (1) the shape and dimensions of the magnetic islands in the x, y, and z directions; (2) the length of the gap between adjacent islands, i.e., the spacing of the islands in the x dimension; (3) the distance between rows of islands in the y dimension. Although these parameters are interrelated, they are discussed separately below for convenience. Other considerations, also addressed below, include the material structure of the magnetic regions and the trapping energy for a magnetic particle.

(1) Shape and Dimensions of Magnetic Islands

Although FIGS. 2 and 3 illustrate a regular arrangement of diamond-shaped magnetic islands, it will be appreciated that the shape and size of the islands may vary as may the spatial relationship between the islands. The islands may be, for example, ovals, rectangles, diamonds, lozenges, polygons, variations on the preceding shapes, etc. In certain embodiments of the invention the islands are oblong. By oblong is meant a shape in which the length and width (i.e., the dimensions in the x and y directions) are not equal. For descriptive purposes, it will be assumed that the length refers to the dimension in the x-direction while the width refers to the dimension in the y-direction as shown in FIGS. 2 and 3. Thus the islands depicted in FIGS. 2 and 3 are oblong, with a length $l_{is}$ greater than their width $w_{is}$. Under such conditions each island has ends with opposite magnetic polarities when magnetized. Facing ends of adjacent oblong magnetic islands form a localized field 50 as shown in FIG. 3.

Figure 4:
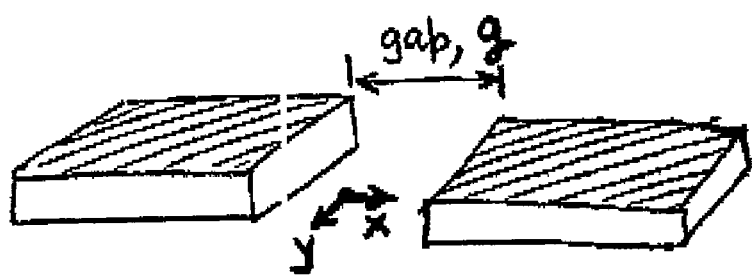
FIG. 4 shows another schematic view of two adjacent magnetic islands separated by a gap of width g.

FIG. 4 shows another schematic view of two adjacent magnetic islands separated by a gap of width g. Referring to this figure, the strength of the localized magnetic field H(x,y) produced by the two islands may be approximated as follows (assuming that the width of the gap is constant in the y dimension):

$$H(x,y) = -\nabla \Phi(x,y)$$

$$H_x(x,y) = (H_g/\pi)\tan^{-1}[y/(x^2+y^2-\tfrac{1}{4})]$$

$$H_y(x,y) = (-H_g/2\pi)\ln[((x+\tfrac{1}{2})^2+y^2)/((x-\tfrac{1}{2})^2+y^2)] \quad \text{(Eq. 1)}$$

Figure 5:
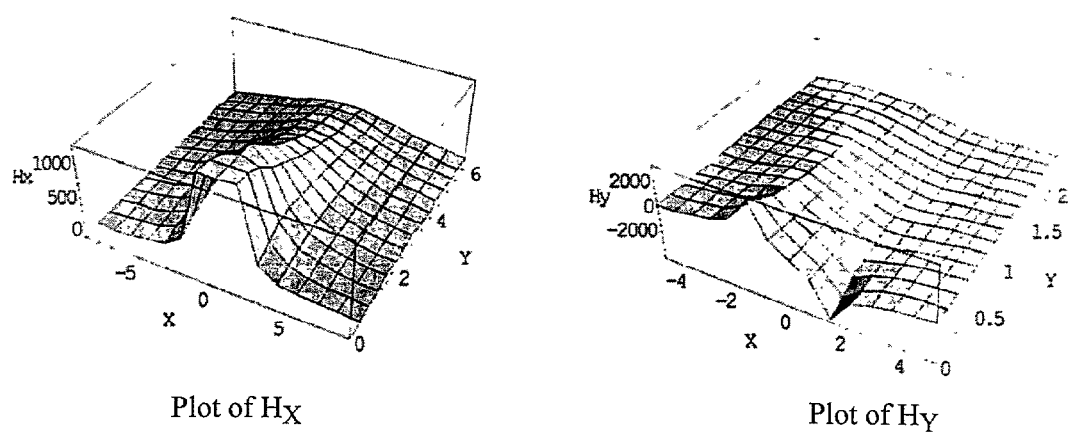
FIG. 5 shows the calculated magnetic field strengths in the x and y directions, assuming a 3 μm gap spacing (g=3 μm) and rectangular cobalt islands.

In the above equations H stands for magnetic field, $\Phi$ stands for magnetic potential, and $H_g$ stands for the saturation field for the magnetic material. x and y are in units of the gap, i.e., a distance equivalent to the width g of the gap has a value of one gap unit. This equation may be used to roughly calculate the strength of the field within the gap and outside the gap. Note that this equation is approximate only, and the exact form of the equation depends upon the geometry of the gap. A more accurate calculation of the magnetic field strengths may be obtained using numerical modeling. For example, the Mathematica® program (and other similar programs) may conveniently be used to model the localized magnetic field produced by magnetic region and gap configurations of different shapes and sizes. One of ordinary skill in the art will readily be able to generate and use such models. FIG. 5 shows the calculated magnetic field strengths in the x and y directions, assuming a 3 μm gap spacing (g=3 μm) and rectangular cobalt islands. As shown in FIG. 5, the field strengths are on the order of 1000 Gauss in the gap region. The magnetic field in the x-direction (pole to pole) is relatively constant and strong in most of the gap, trailing off rapidly outside the gap. The field in the y-direction (both in and out of the gap) is mostly due to the fringing field and averages to zero when integrated over the gap region. The trailing fields outside the gap region have an impact when the magnetic bead is in the process of being trapped, as it diffuses in the vicinity of a gap. Once trapped in the gap, the permeability of a magnetic particle will collapse the field lines mostly into it, leaving a negligible trailing field outside the gap to attract a second bead to the same (filled) gap region.

Figure 6:
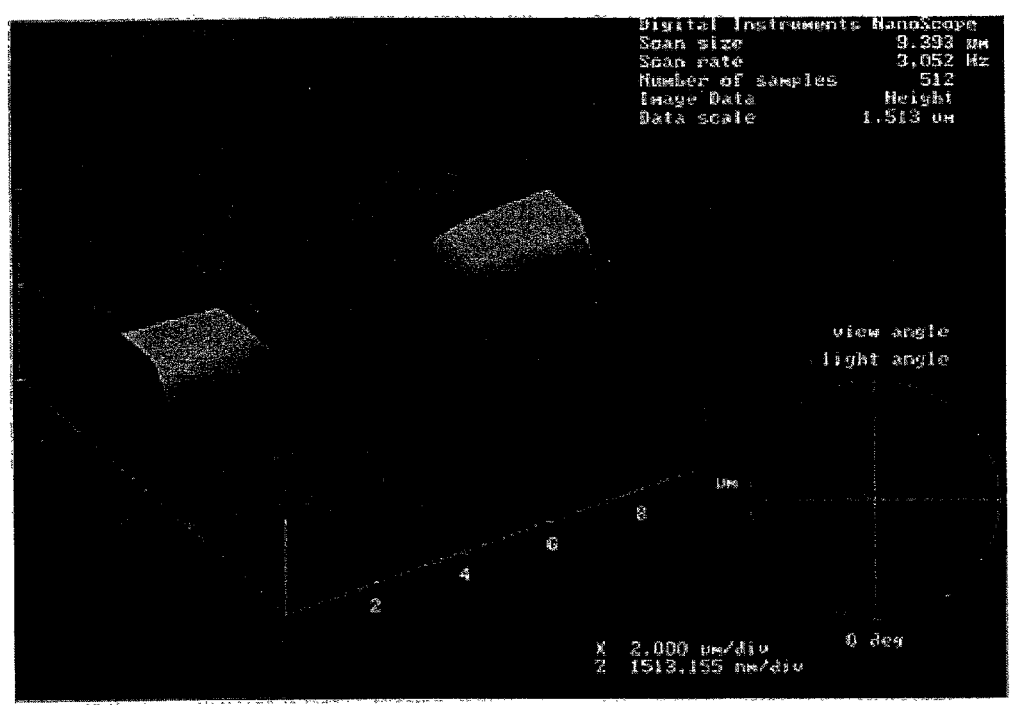
FIG. 6 shows an Atomic Force Microscope (AFM) image of portions of two adjacent magnetic islands and the gap between them according to one embodiment of the invention. In this figure the length of the gap is approximately 3 μm and the width in the y dimension (i.e., the distance between the longer faces of the islands) is on the same order.

As is evident from the foregoing discussion, the absolute and relative strengths of the fields within and outside the gap influence the likelihood that one or more beads will be trapped in or adjacent to the gap. Generally it is desired that only a single bead be trapped in each gap. Accordingly, it may be desirable to select island geometries and spacings that result in a strong field within the gap and a weaker field outside the gap. For example, magnetic field calculations showed that diamond-shaped islands resulted in a strong field within the gap. However, these islands also produced a region of "fringing" field outside the gap, which increased the likelihood of trapping additional beads in the region around the gap. Magnetic islands with a substantially rectangular shape or a rectangular shape with rounded corners or flattened corners (similar to a bar magnet) resulted in reduced fringing fields. FIG. 6 shows an Atomic Force Microscope (AFM) image of portions of two adjacent magnetic islands and the gap between them according to one embodiment of the invention. In this figure the length of the gap is approximately 3 μm and the width in the y dimension (i.e., the distance between the longer faces of the islands) is on the same order.

The width $w_{is}$ of the islands is also significant in terms of the likelihood of trapping one or more beads within or adjacent to a gap region. If the width is too great the fringing field may trap additional beads adjacent to a filled gap region. If the width is too small, the field within the gap is reduced and may not be strong enough to efficiently trap a bead in the gap region. The dimensions of the magnetic particles to be used with the chip influence the optimum selection of island width. In certain embodiments of the invention the island width is selected to be approximately the same as the diameter of a spherical bead. For example, if 2.8 μm diameter beads are to be used, an island width of 3 μm may be selected. In certain embodiments of the invention the island width is between 1 and 10 μm, between 1 and 5 μm, between 5 and 10 μm, between 10 and 15 μm, or between 15 and 20 μm. In certain embodiments of the invention the island width is selected to be approximately the same as the diameter of a spherical bead. For example, if 2.8 μm diameter beads are to be used, an island width of 3 μm may be selected. One of ordinary skill in the art will be able to select an appropriate value of w, taking into consideration the dimensions of the magnetic particle and the other dimensions of the islands and gap regions.

Figure 7:
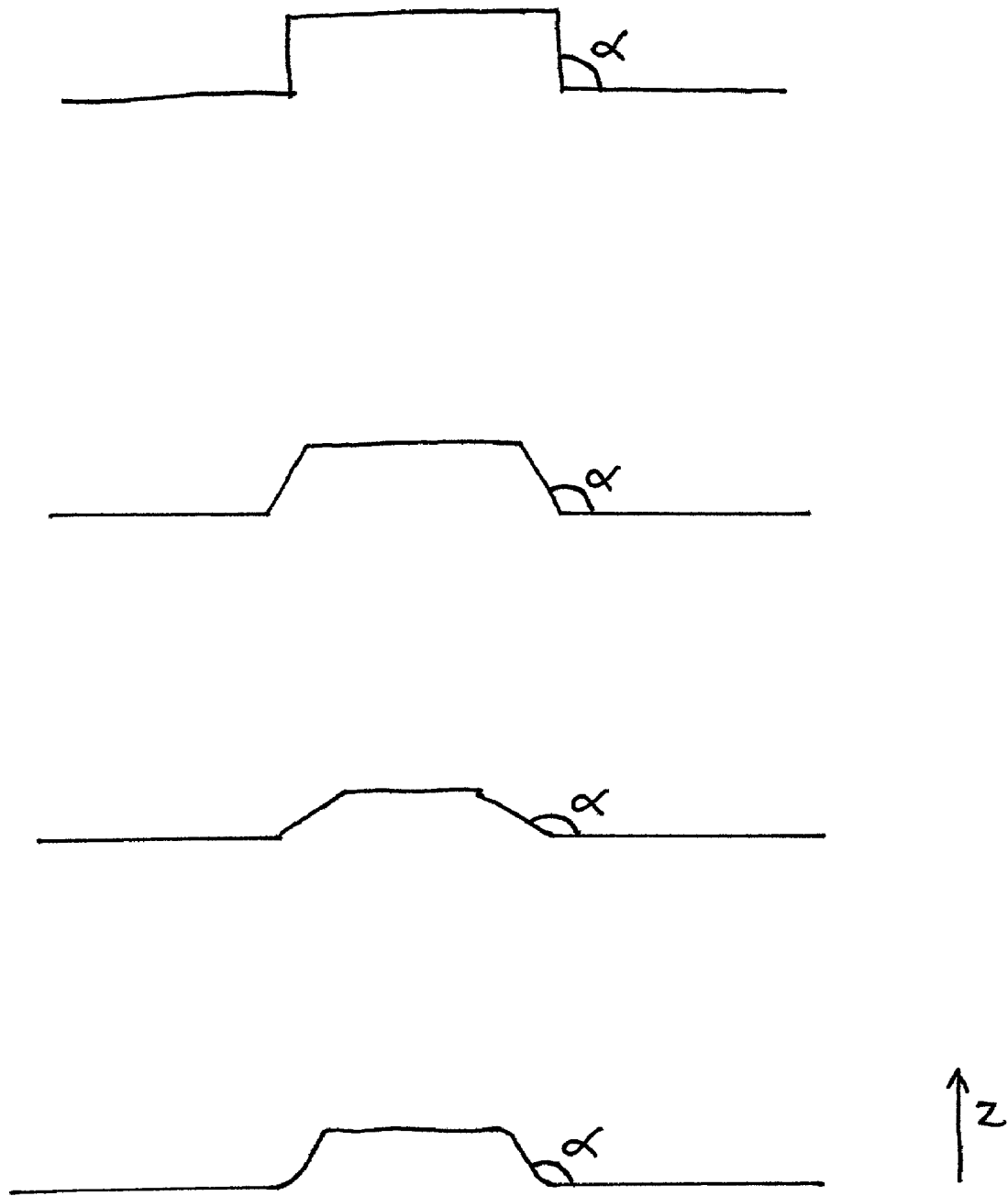
FIG. 7 shows a schematic cross-sectional view of several islands with different vertical profiles, where the angle between the island wall at the gap and the substrate is indicated as α.

The vertical profile of the islands (i.e., their profile in the z-dimension) is also a significant design consideration, particularly at the edges of the gap where the magnetic particles are trapped. FIG. 7 shows a schematic cross-sectional view of several islands with different vertical profiles, where the angle between the island wall at the gap and the substrate is indicated as α. In certain embodiments of the invention the wall is substantially vertical (i.e., perpendicular to the plane of the substrate), while in other embodiments of the invention the wall forms an angle α of greater than 90° with the substrate. The angle may be between 90 and 100 degrees, between 100 and 110 degrees, between 110 and 120 degrees, between 120 and 130 degrees, between 130 and 140 degrees, between 140 and 150 degrees, etc. Of course the angle may also be less than 90°. In addition, the angle may vary in the vertical dimension. The walls may not meet to form an angle with straight edges but rather may form a curve, in which case the angle will be approximate. A substantially vertical wall may result in better particle trapping than an angled wall. The angle of the wall may vary depending on the etching technique. One of ordinary skill in the art will be able to vary the etching parameters and technique to generate a substantially vertical or angled wall as desired.

The length $l_{is}$ of the magnetic islands may also be varied. It will be appreciated that the length may be selected in conjunction with the width of the islands and the gap length in order to minimize fringing fields. In certain embodiments of the invention the islands are substantially rectangular, and the length l is approximately equal to the width $w_{is}$. In certain embodiments of the invention the islands are substantially rectangular, and the length $l_{is}$ is greater than the width $w_{is}$ by a factor of between 1 and 2. In certain embodiments of the invention the islands are substantially rectangular, and the length $l_{is}$ is greater than the width $w_{is}$ by a factor of between 2 and 3. In certain embodiments of the invention the islands are substantially rectangular, and the length $l_{is}$ is greater than the width $w_{is}$ by a factor of between 3 and 5. In certain embodiments of the invention the islands are substantially rectangular, and the length $l_{is}$ is greater than the width $w_{is}$ by a factor of between 5 and 10. These relative dimensions are merely exemplary and are not intended to limit the invention in any way.

Where the island is not rectangular, there may be a minimum and a maximum width and/or length, depending on the points at which the measurement is made. For example, in FIG. 3, the minimum length of an island is indicated by $l_{min}$ while the maximum length is indicated by $l_{max}$. In certain embodiments of the invention the maximum length of the island is approximately equal to the maximum width of the island. In certain embodiments of the invention the maximum length of the island is greater than the maximum width of the island. The relative length and width may have any of the relationship listed above for the case of rectangular islands.

It will be appreciated that island length and also the spacing between rows of islands in the y-dimension (indicated as s in FIG. 3) influence the array density (i.e., the density of attachment locations). For example, if an island row spacing (i.e., the distance between the center in the y-dimension of islands in adjacent rows) of approximately 20 μm and an island length of approximately 17 μm are selected, the array density will be approximately 2500 sites/mm$^2$ (assuming a gap of 3 μm, which results in a site-to-site spacing of 20 μm in the x-dimension). If an island length and row spacing of approximately 10 μm is selected the array density will be approximately 10,000 sites/mm$^2$. These dimensions are readily achievable. In certain embodiments of the invention the island length is between 30 and 100 nm. In certain embodiments of the invention the island length is between 100 and 500 nm. In certain embodiments of the invention the island length is between 500 nm and 1000 nm. In certain embodiments of the invention the island length is between 1 and 5 μm. In certain embodiments of the invention the island length is between 5 and 10 μm. In certain embodiments of the invention the island length is between 10 and 20 μm. In certain embodiments of the invention the island length is between 20 and 30 μm. In certain embodiments of the invention the island length is between 30 and 50 μm. The distance between rows of islands may fall within any of the foregoing dimensions. It will be appreciated that the island length and spacing may be appropriately selected based upon the dimensions of the magnetic particle to be used. For example, where a 2.8 μm bead is used and a gap length and island width of approximately 3 μm are selected, an island length of less than 3 μm may lead to undesirably large fringing fields.

(2) Gap Length and Width

The trapping of the magnetic beads on the chip can be optimized by choosing appropriate island geometries and appropriate spacing between adjacent islands in both an x and y dimension. The spacing, shape, and size of the islands and gaps between them can be selected to strongly attract (and ultimately trap) a single magnetic bead. It will be appreciated from the above discussion that the selection of appropriate island and gap dimensions is interdependent. In general, the optimum spacing and size of the islands and gaps depends on the size of the beads to be used. Using 2.8 μm diameter beads and chips created with gap spacing varying from approximately 1 μm to approximately 5 μm, it has been found that if the gap is too small the efficiency of trapping is reduced. If the gap is too large, multiple beads may be trapped at each site. Experiments have suggested that a gap length slightly larger (in the x-dimension) than the bead diameter provides good results. In certain embodiments of the invention the minimum spacing between adjacent islands (indicated with the symbol g for gap) is between 1 and 5 microns. In certain embodiments of the invention the minimum spacing between ends of adjacent islands is between 1 and 10 microns. In certain embodiments of the invention the spacing between ends of adjacent islands is between 5 and 15 microns. In certain embodiments of the invention the minimum spacing between ends of adjacent islands is approximately 3 microns. One of ordinary skill in the art will appreciate that smaller or larger gap spacings may be appropriate for smaller or larger diameter beads. In certain embodiments of the invention the maximum dimension of the gap is approximately equal to the maximum dimension of a magnetic particle (e.g., the diameter of a spherical particle). The maximum dimension of the gap may be, for example, within 1%, within 5%, within 10%, within 20%, within 30%, within 50%, within 75%, within 100% greater than the maximum dimension of a particle. Other dimensions may also vary and may be approximately the size of the maximum dimension of a particle. Certain of the dimensions of the gap may be larger or smaller than the dimensions of the particle.

Figure 8:
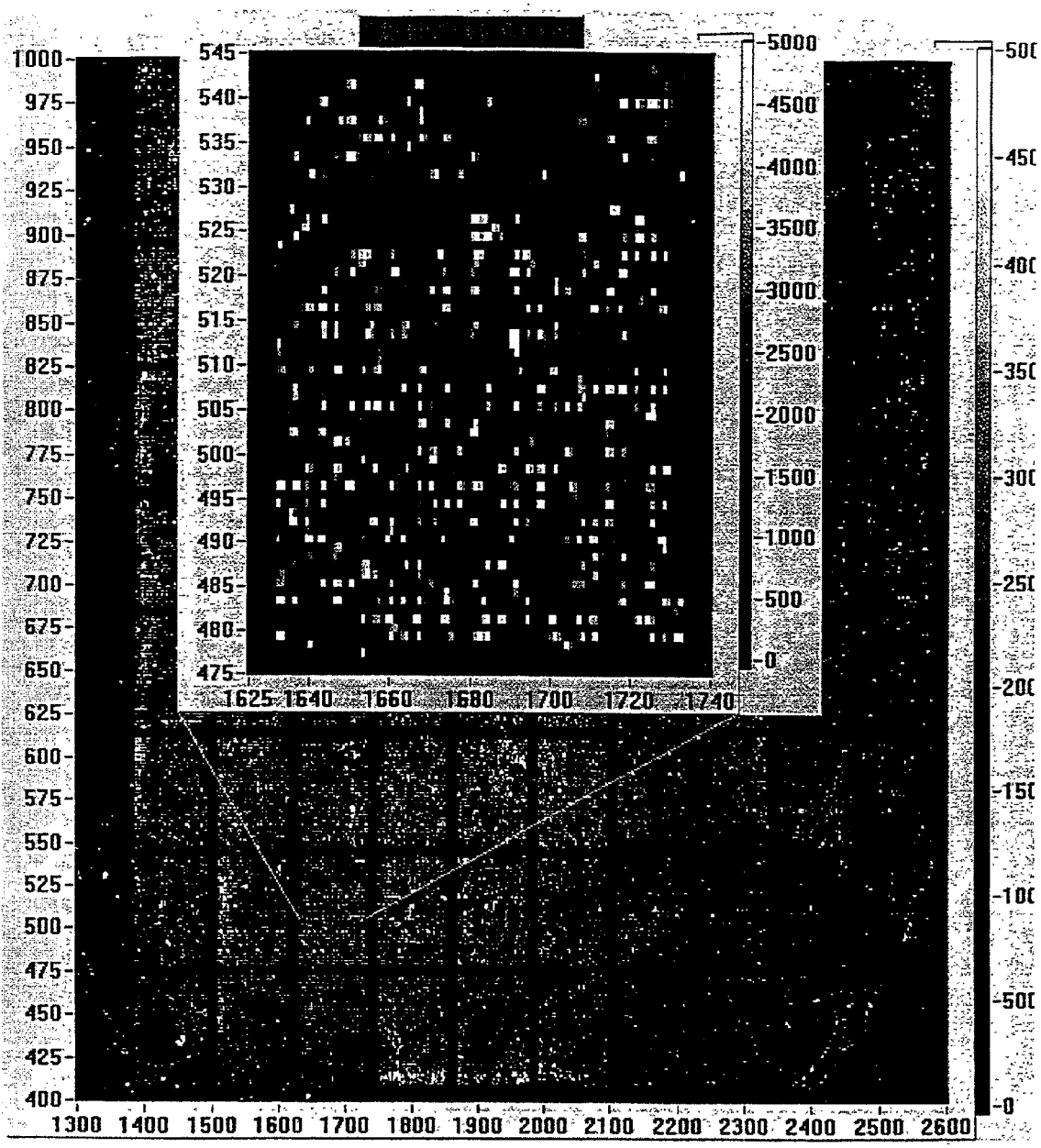
FIG. 8 is a fluorescence image obtained (after arraying fluorescently labeled beads) from a 10×10 array of arrays, where each of the 100 subarrays contains a 30×30 pattern of magnetic islands. The inset shows an enlarged view of one of these subarrays, containing a 30×30 pattern of magnetic regions. The vertical scale in the image is 20 μm/count. Thus the inset shows a section of the chip 70 counts=1400 μm in length.

The effect of gap length on bead trapping is demonstrated in Example 2, which describes arraying of beads on a magnetic chip fabricated as an array of arrays, where the length of the gaps in each subarray increases from 1 to 4 μm across the chip (in a right to left direction as viewed in the fluorescence scan in FIG. 8. As can be seen from FIG. 8, too small a gap between magnetic domains results in low trapping efficiency. Too large a gap allows trapping of multiple beads at some attachment locations.

It will be appreciated that the magnetic islands may have pointed or partially tapered ends or flat ends as shown in FIGS. 2 and 3. In this case the distance between adjacent ends will depend on where in the y dimension the measurement is made. However, it will be possible to ascertain the minimum spacing between the ends, i.e., the distance in the x-dimension that separates the closest portions of two adjacent islands. As will be evident, the optimal spacing may vary depending on the size of the beads for which the chip is designed. For example, if a chip is to be used with 2.8 micron beads the spacing between ends of adjacent islands may be less than if the chip is to be used with 5 or 10 micron beads.

The gap width (i.e., the gap dimension in the y direction) is determined by the width of the magnetic islands, which has been discussed above.

(3) Distance Between Rows of Islands in the y Dimension

As discussed above, the length of the islands (as well as the length of the gap) influences the array density. In addition, the distance between rows of islands in the y dimension influences the array density with a smaller distance between rows resulting in a higher density of attachment sites. In certain embodiments of the invention the rows of islands are separated from each other by a distance equal to or greater than the width of the islands themselves in order to minimize interaction between localized magnetic fields produced by islands in adjacent rows.

(4) Magnetic Island Structure

As discussed above, in certain embodiments of the invention it is desirable to tailor the size, shape, and spacing of the islands to increase the likelihood of trapping one and only one bead within or adjacent to a gap region. Single bead capture is enhanced if the magnetic field in the gap is such that it permeates a single bead almost completely (i.e., such that the magnetic field lines are confined primarily to within the bead), leaving very little fringing field to bind additional beads. In the plane of the substrate, this issue may be addressed by tailoring the island and gap geometries as discussed above. In the vertical dimension, to center the field on a bead of approximately 2.8 μm diameter it would be desirable to have a magnetic island approximately 3 μm in height. However, it can be time consuming in fabrication to sputter deposit a layer of magnetic material more than about 1 μm in thickness. To address this issue, in certain embodiments of the invention a layer of nonmagnetic material, is sandwiched between the magnetic material and the substrate surface. For example, a layer of nonmagnetic material (e.g., a layer of $SiO_2$ approximately 1-2 μm thick for an array designed for 2.8 μm diameter beads) is deposited on the substrate using any appropriate technique, e.g., sputtering. Then a layer of magnetic material (e.g., cobalt, approximately 1 μm thick for an array designed for 2.8 μm diameter beads) is deposited on top of the nonmagnetic layer. The subsequent processing steps remain the same as described above. When etching is used, it may be desirable to select an etching method (or combination of etching methods) that will etch both the nonmagnetic and magnetic materials. The process of using a first etch for cobalt and then a second for silicon dioxide is straightforward to those skilled in the art. However, any of a number of nonmagnetic and magnetic materials could be used. The thickness of the nonmagnetic layer may be selected as appropriate for the size of bead to be arrayed, the desired height of the magnetic islands, etc.

It will be appreciated that the foregoing approach is not limited to application of a single layer of nonmagnetic material below the magnetic material. Any number of layers of nonmagnetic and/or magnetic material could be applied. In addition, the thickness of the layers may be such that the bead is actually suspended above the chip surface. For example, a nonmagnetic layer of approximately 2 μm thickness below the magnetic layer would likely result in a suspended bead. This may be understood as follows. The weight, or gravitational force F on the bead is given by the following equation:

$$F = mg1.4 \times 10^{-13} \text{ Newtons} \qquad (\text{Eq. 5})$$

where m=mass of bead, acceleration due to gravity 9.8 m/s². The mass of an M-280 Dynabead (as provided by the manufacturer) is $1.4 \times 10^{-14}$ kg). Assuming that the magnetic field of the gap drops off to zero over 10 μm, the magnetic force holding up the bead is approximately $7 \times 10^{-10}$ N, which is several thousand times the bead weight. (Calculation of the magnetic force on the bead is discussed below.) Having the bead suspended may offer advantages in terms of better accessibility to reagents, wash solutions, and samples (e.g., better accessibility to nucleic acid hybridization targets) than if it sits on the surface.

It will be appreciated that many of the above dimensions and calculations relevant to chip design will vary with the size of the magnetic particle. In general, dimensions and other features will scale according to the dimensions of the magnetic particles, e.g., the diameter of spherical magnetic beads.

(5) Flux Circulator

Figure 13:
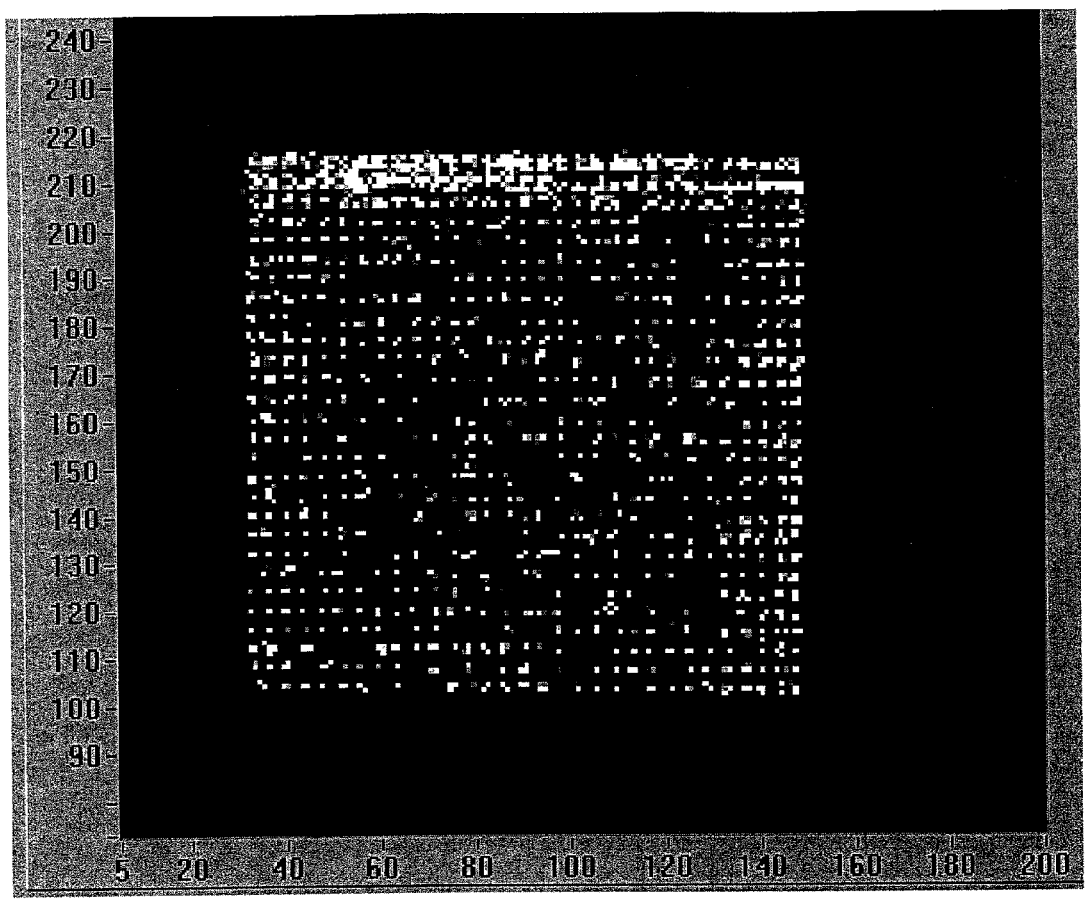
FIG. 13 shows a fluorescence image obtained after performing a DNA hybridization assay on magnetic beads and then arraying the beads on a magnetic chip.
Figure 14:
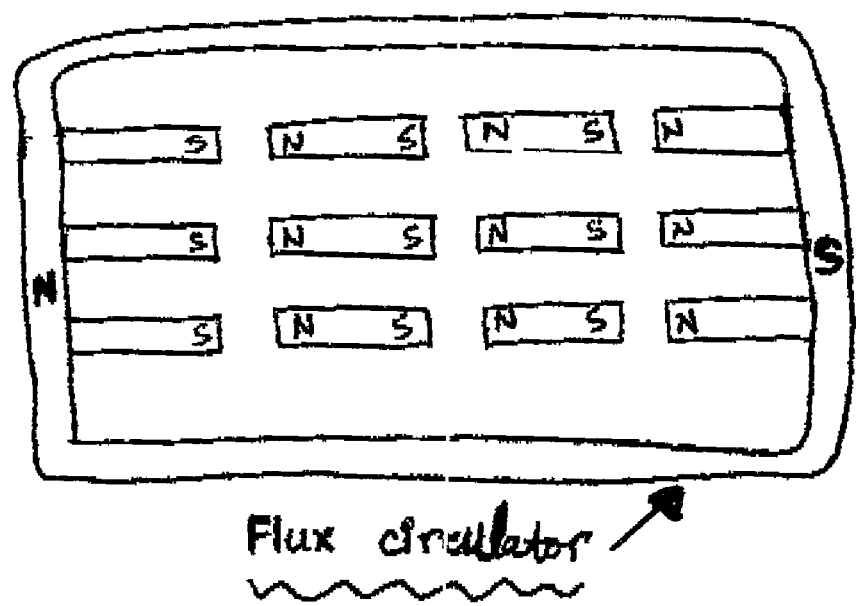
FIG. 14 shows a schematic view of a flux circulator positioned to reduce fringing fields at the edges of an array.

As described herein, fringing fields and/or magnetic fields other than the localized magnetic fields themselves may contribute to clumping of beads on the array and/or trapping of zero or of multiple beads at a given attachment location rather than trapping of a single bead. Such effects may be seen in FIG. 13, where clustering of multiple beads is evident at the top of the array while sites at the center of the array are more sparsely populated (i.e., a number of sites are unoccupied). While not wishing to be bound by any theory, these effects may be due to the existence of a magnetic field extending between opposite ends of the entire array or subarray, e.g., between the top and bottom of the array as seen on FIG. 13. This may occur because the north and south poles of each magnetic domain at the edges of the array contribute to formation of a more "global" north and south pole that extends between opposite edges of the array as a whole. This field has a gradient that results in a force on the magnetic particles. According to certain embodiments of the invention such an effect can be minimized by including a flux circulator in the magnetic device, as pictured in FIG. 14. The flux circulator may comprise a loop that extends around the edges of the chip, allowing the magnetic field lines to circulate therein. The flux circulator may comprise a magnetic material, e.g., cobalt, and can be readily fabricated using the same techniques as those used to fabricate the other elements of the device. Thus the invention may include a flux circulator. In certain embodiments of the invention the flux circulator extends around the edges of the magnetic chip and connects opposite poles of the magnetic regions as depicted in FIG. 14.

(6) Array of Arrays

The magnetic chip can comprise a plurality of individual arrays or subarrays of attachment locations. Such an arrangement of multiple subarrays is referred to as an array of arrays configuration. The subarrays can be (but need not be) present in a regular arrangement, as shown in FIG. 8, which is a fluorescence image obtained (after arraying fluorescently labeled beads) from a 10×10 array of arrays, where each of the 100 subarrays contains a 30×30 pattern of magnetic islands. The individual subarrays can be separated, e.g., by hydrophobic boundaries or by components of a bonded microfluidic assembly.

The overall layout of the chip may be determined by the study size. For instance, a genotyping study involving relatively few markers (probes) and many samples, e.g., 100 markers and 1000 samples to be analyzed may advantageously employ a chip layout where there are approximately 1000 sites per subarray (providing 10-fold redundancy) and a 1000 array of arrays chip design. This design would allow each sample (e.g., a sample from a single individual) to be interrogated in its own array simultaneously. A study which involves more markers with fewer samples may advantageously employ a chip layout where there are approximately 10,000 sites per array with fewer individual subarrays. When an array of arrays configuration is used a microfluidic assembly is convenient for introducing different bead populations and/or samples to each of the subarrays.

Figure 9:
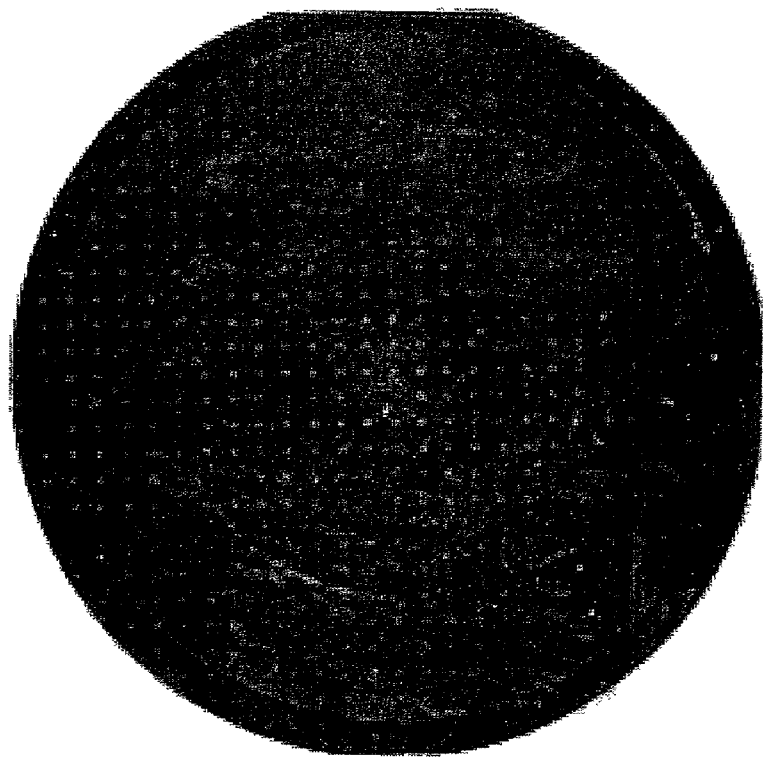
FIG. 9 shows an image of an entire magnetic wafer patterned with an array of subarrays. The chip is approximately 3 inches in diameter and contains well over 500 subarrays at a spacing of approximately 0.1 inch in each direction. Each subarray (details not visible in image) contains a 30×30 pattern of magnetic islands such as those shown in the AFM image of FIG. 6.

FIG. 9 shows an image of an entire magnetic wafer patterned with an array of subarrays. The chip is approximately 3 inches in diameter and contains well over 500 subarrays at a spacing of approximately 0.1 inch in each direction. Each subarray (details not visible in image) contains a 30×30 pattern of magnetic islands such as those shown in the AFM image of FIG. 6. Thus each subarray contains approximately 900 attachment sites. An experiment involving the analysis of 100 genomic markers on each of 500 different individuals could be performed in one run on this wafer (assuming 9-fold redundancy).

(7) Alternative Designs

It will be appreciated that a number of alternative design approaches are possible and fall within the scope of the invention. For example, a substrate having magnetic regions and nonmagnetic islands could also be used. In such a design one or more surfaces of the gap between the islands comprises or sits above a magnetic material, thereby forming a magnetic well in which a magnetic particle can be trapped. Alternatively, a flat substrate comprising magnetic and nonmagnetic materials could be used. In some embodiments of the invention the magnetic material regions need not be separated with a nonmagnetic material. For example, the surface of the chip may be similar to a computer hard disk, having a pattern of magnetization written on it such as those used to indicate 0's and 1's on a hard disk. The areas of 0's and 1's can be provided in a conventional fashion.

Figure 15:
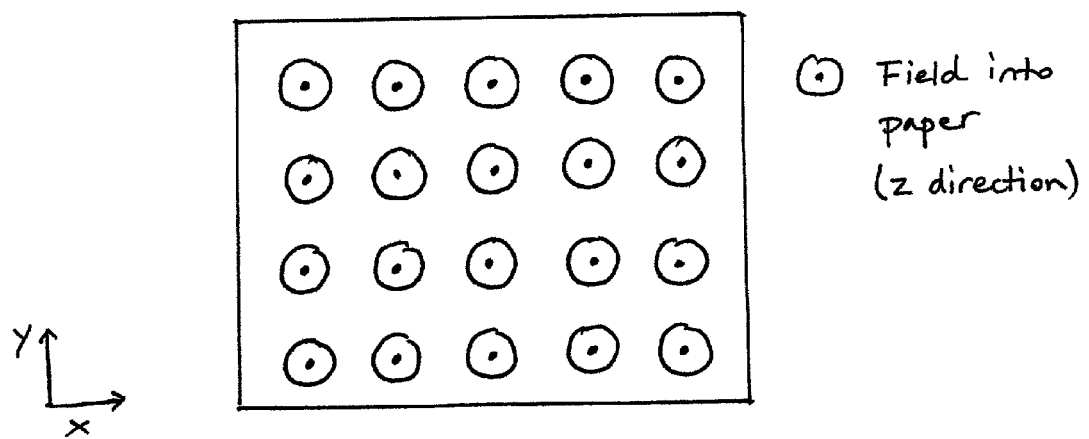
FIG. 15 shows a schematic view of an alternate chip design employing localized magnetic fields extending between opposite poles of individual magnetic regions.

According to certain embodiments, the localized magnetic fields extend between opposite poles of individual magnetic regions rather than between opposite poles of adjacent magnetic regions. FIG. 15 shows a schematic view of such a chip design employing localized magnetic fields extending between opposite poles of individual magnetic regions having a circular cross-section. On this figure, magnetization is in the z-axis, i.e., perpendicular to the plane of the paper. In those embodiments of the invention in which localized magnetic fields extend between opposite poles of single magnetic regions rather than between opposite poles of two magnetic regions, the descriptions herein that refer to the space, region, or volume between two magnetic regions generally apply to the volume between opposite poles of a single magnetic region where relevant in the context of the description.

While varying in configuration, the embodiments described above incorporate the common feature of producing localized magnetic fields within or between magnetic regions, where the localized magnetic fields are sufficient to immobilize (trap) a magnetic particle. In other words, the localized magnetic fields produce forces that are of sufficient strength to result in a trapping energy that is significantly greater than the thermal energy of the particle (e.g., 2-fold greater, 3-fold greater, 5-fold greater, 10-fold greater, 100-fold greater, 1,000-fold greater, 10,000-fold greater, etc.), so that thermal motion (diffusion) has essentially no impact on the bead position once it is trapped by the field. Trapping energy is discussed further below.

B. Materials (1) Substrate

Any of a variety of materials may be used for the substrate. In embodiments of the invention where the substrate is non-magnetic, silicon is a convenient choice. Other suitable materials include ceramics, glass, metals such as platinum or gold, or polymeric materials such as plastics. In certain embodiments of the invention it may be desirable to fabricate the substrate from a transparent material or to incorporate a transparent material (e.g., glass or plastic) into the substrate beneath the gap regions to allow optical detection from underneath the fabricated chip. In certain embodiments of the invention, e.g., for applications involving biomolecules, it is desirable that regions of the chip that will contact probe and/or target be biocompatible. If a non-biocompatible material is used, it may be coated with a suitable biocompatible material.

(2) Magnetic Regions

In certain embodiments of the invention the magnetic regions are made of or comprise a ferromagnetic material such as cobalt. Other ferromagnetic materials such as magnetizable ceramics, iron, nickel, or nickel-iron alloys could also be used. However, since iron or ferrite is toxic to certain biomolecules such as DNA, it is desirable to coat iron-containing materials with a biocompatible material. As mentioned above, when the magnetic regions are islands, a portion of the island may be magnetic while the remainder of the island is made of a nonmagnetic material.

C. Fabrication

Figure 10:
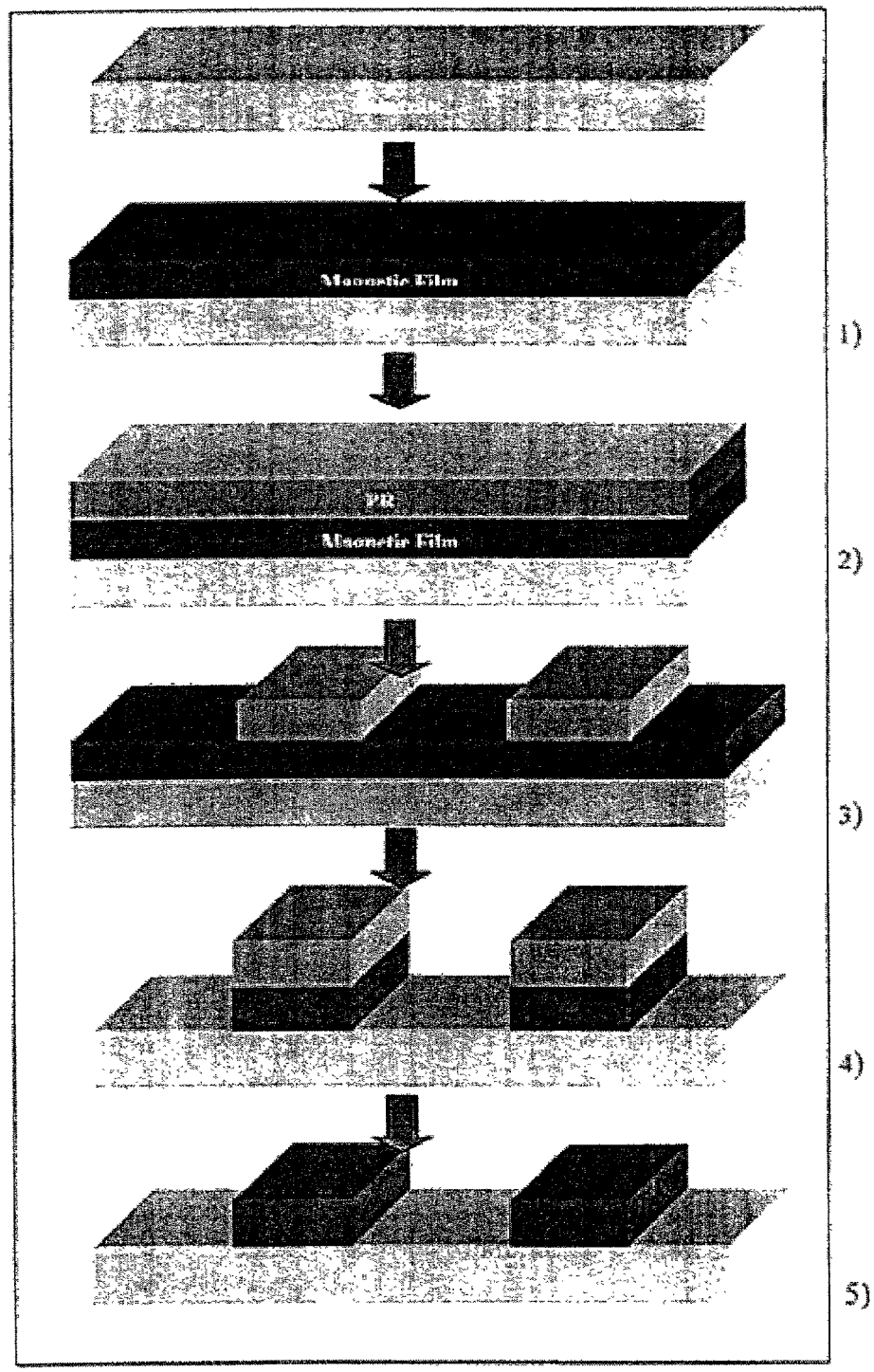
FIG. 10 shows process steps according to one method for fabricating a magnetic chip of the invention.

In certain embodiments of the invention the chip comprises a regular two-dimensional array of magnetic material regions formed on a non-magnetic substrate. The magnetic regions may be formed using any of a variety of processes. In particular, the fabrication process may employ photolithographic techniques that are well known in the field of integrated circuit technology (See, e.g., Campbell, S., *The Science and Engineering of Microelectronic Fabrication*, Oxford University Press, New York: 1996). The process may be additive or subtractive in nature. One example of a subtractive process is depicted in FIG. 10. As shown in the figure (step 1) a layer of magnetic material such as cobalt, referred to as a magnetic film, may be deposited on a substrate. The layer may be of any appropriate thickness, e.g., between 0.1 and 0.5 µm, between 0.5 and 1.0 µm, between 1.0 and 2.0 µm, between 2.0 and 3.0 µm, between 3.0 and 5.0 µm, etc. A typical width is between 0.7 and 1.0 µm. Thinner layers may also be used, in particular for applications involving nanometer scale magnetic particles. In general, the thickness of the layer may be selected according to the size of the magnetic particles to be trapped and the geometry selected for the magnetic regions and gaps, as described above.

Figure 11:
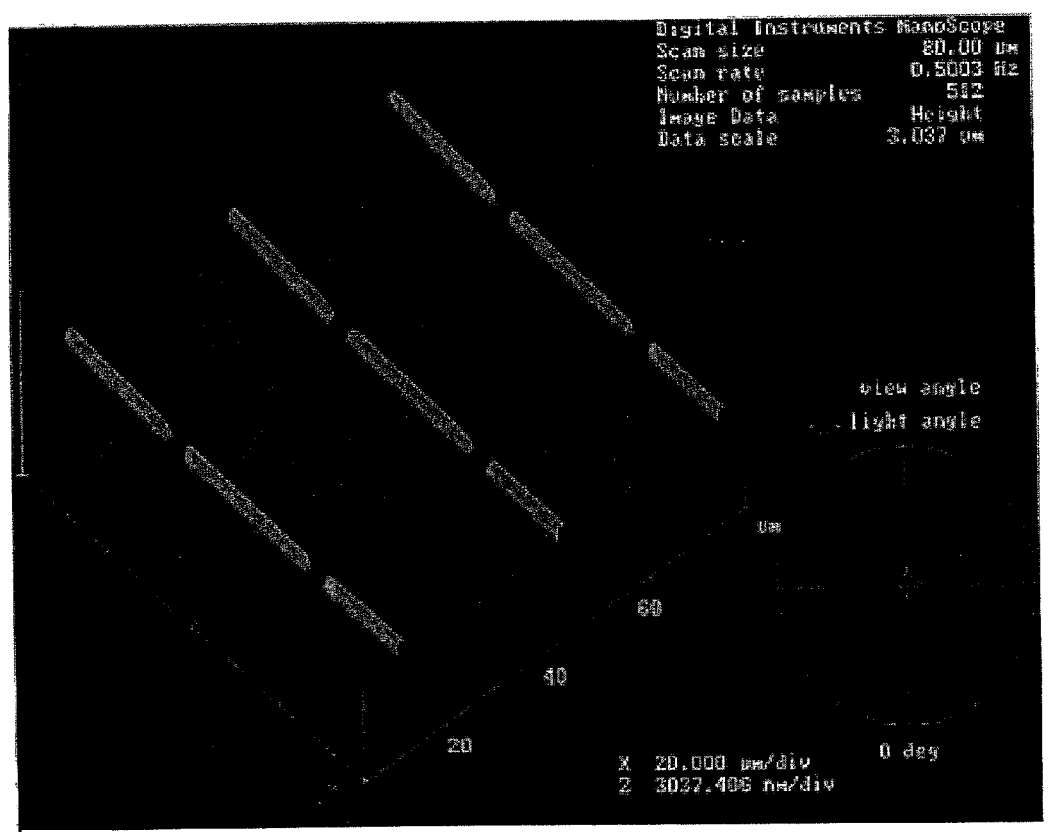
FIG. 11 shows an AFM image of a portion of a magnetic chip fabricated according to the foregoing process. The scale is in tens of microns, showing the gap sites to be approximately 30 μm apart in both x and y dimensions.

Any suitable deposition process including sputtering (e.g., argon sputter etching using a UHV DC magnetron sputtering system) or evaporation can be used. A layer of photoresist (PR) is then applied onto the layer of magnetic material as shown in Step 2 of FIG. 10. The photoresist is then patterned according to conventional methods (e.g., exposed to e-beam or optical lithography and developed as shown in Step 3) to generate a mask. Then the magnetic material is etched (e.g., using argon sputter etching using an ion-milling etcher) through the regions exposed by the developed photoresist as shown in Step 4. Ion beam etch or plasma etch processes allow the formation of magnetic regions with substantially vertical side walls, as is desirable in certain embodiments of the invention. The photoresist is then stripped, leaving the magnetic islands projecting above the substrate (Step 5). Finally, the magnetic islands are magnetized along a chosen axis at a field sufficient to ensure saturation. For example, a field of several thousand Gauss is sufficient to saturate cobalt. FIG. 11 shows an AFM image of a portion of a magnetic chip fabricated according to the foregoing process. The scale is in tens of microns, showing the gap sites to be approximately 30 µm apart in both x and y dimensions. The elongated, rectangular-shaped magnetic islands projecting above the substrate surface are clearly visible.

In an example of an additive process, a layer of photoresist is deposited on a substrate and exposed to form a pattern of apertures. A magnetic material is deposited within the apertures (e.g., by vapor deposition) and the photoresist is then removed to leave islands of magnetic material on the substrate.

As will be evident to one of ordinary skill in the art, a number of variations on the above processes may be used. In general, selection of appropriate processes may depend upon the exact chip configuration selected (e.g., whether the magnetic regions are islands or are flush with the substrate or present in wells). Although semiconductor manufacturing technologies such as those described above are convenient, well developed, and readily scalable, other types of processes may also be employed.

D. Trapping Energy and Localized Magnetic Fields

As discussed above, the magnetic chip concept involves the use of magnetic regions to produce localized magnetic fields of appropriate strength and shape to reversibly immobilize (trap) magnetic particles. The force on the magnetic particle is determined by the gradient of the magnetic field times the magnetization of the particle. Thus a localized magnetic field has a gradient sufficient to generate a localized force on a magnetic particle that results in trapping. The localized magnetic field results in a force in the direction in which the gradient is greatest. This force tends to pull a magnetic particle in such a direction. Trapping efficiency may be enhanced if the localized magnetic field falls off rapidly outside the volume where the magnetic particle is to be trapped. In certain embodiments of the invention the localized magnetic field decreases to less than half, less than 25%, less than 10%, less than 5%, less than 2%, or less than 1% of its maximum value within a distance equal to the maximum dimension of either the volume between two adjacent magnetic regions (in those embodiments of the invention where the localized magnetic fields extend between opposite poles of adjacent magnetic regions) or the volume of a single magnetic region (in those embodiments of the invention where the localized magnetic fields extend between opposite poles of individual magnetic regions. In certain embodiments of the invention the force on a magnetic particle decreases to less than half, less than 25%, less than 10%, less than 5%, less than 2%, or less than 1% of its maximum value within a distance equal to the maximum dimension of either the volume between two adjacent magnetic regions (in those embodiments of the invention where the localized magnetic fields extend between opposite poles of adjacent magnetic regions) or the volume of a single magnetic region (in those embodiments of the invention where the localized magnetic fields extend between opposite poles of individual magnetic regions. In certain embodiments of the invention the fringing fields have negligible effect on the arraying behavior of magnetic particles.

The strength of trapping of the magnetic particles is determined by the magnetic field profile at the attachment locations (e.g., at the gap between magnetic islands in the embodiment described above) and may be expressed in terms of the trapping energy. The trapping energy may be thought of as the amount of energy that would be required to remove a magnetic particle once it has been trapped. Thus the trapping energy influences both the strength with which a particle is immobilized and the conditions required to remove it.

Writing the magnetization in terms of the volumetric magnetic susceptibility and integrating the force results in an expression for the binding energy. The components of the localized magnetic field H may be calculated as described above. As mentioned previously, $H_y$ integrates to approximately zero over the gap region. $H_z$ may be approximated as zero provided the magnetic regions generating the localized field are substantially equal in terms of geometry and composition. Thus the trapping energy E may be calculated from the following equations:

$$F = M(H_x/z) = (\chi_m)(V)(H_x)(H/z) = (\chi_m)(V)/z(H_x^2/2)$$

$$E = \int F dz = (\chi_m)(V)(H_x^2/2) \quad \text{(Eq. 2)}$$

where $H_x$=magnetic field strength in the x-dimension, V=magnetic particle volume, $\chi_m$=magnetic particle volumetric susceptibility, F is the force on the bead, and E is the trapping energy.

As an example, in certain embodiments of the invention M-280 Dynabead streptavidin beads (Dynal Biotech, Inc., 5 Delaware Drive, Lake Success, N.Y., 11042) are used. These beads have a 2.8 µm diameter and a volume V of $1.15 \times 10^{-11}$ cm$^3$. The manufacturer lists the volumetric susceptibility $\chi_m$ as 0.012 (cgs units). At a field strength of $H_x$=1000 Gauss (e.g., for rectangular cobalt islands with a width of approximately 3 µm separated by a gap of approximately 3 µm in length) the trapping energy is approximately $7 \times 10^{-8}$ ergs=40,000 eV.

The trapping energy may be compared with the thermal energy of the beads. Thermal energy $E_{th}$ is given by the following equation:

$$E_{th} = kT \quad \text{(Eq. 3)}$$

where k is the Boltzmann constant and T is the temperature in degrees Kelvin. Taking k=$1.38 \times 10^{-23}$ Joules/°K and T=300°

K (approximately room temperature), the thermal energy is calculated as approximately $4.1 \times 10^{-21}$ Joules=0.025 eV. Thus it is evident that the trapping energy produced by the localized magnetic fields on the magnetic biochip of the invention is several orders of magnitude greater than the thermal energy. According to certain embodiments of the invention described herein, the trapping energy is approximately a million times greater than the thermal energy. The particles are thus firmly trapped relative to thermal fluctuations. In addition, reactions such as hybridization, PCR amplification, or other reactions that may be performed at temperatures above room temperature will still result in a thermal energy several orders of magnitude lower than the trapping energy. Of course the initial process of the particle finding its way to the area of the localized magnetic field between magnetic regions is influenced by both sample flow and diffusion into that region.

The trapping energy may also be used to estimate the likelihood that a magnetic particle will escape once trapped. The probability of escape is proportional to $e^{(-E/E_{th})}$ where E=trapping energy and $E_{th}$=thermal energy. Thus when the trapping energy is 5 times the thermal energy, the likelihood of escape is approximately 1%; when the trapping energy is 4 times the thermal energy, the likelihood of escape is approximately 2%; when the trapping energy is 3 times the thermal energy, the likelihood of escape is approximately 5%. The trapping energy decreases linearly with volume of the magnetic particle. Thus for nanoparticle (e.g., a spherical particle of approximately 30 nm diameter), the trapping energy is still greater than the thermal energy.

The preceding calculations suggest that even magnetic trapping fields far weaker than those generated by the magnetic islands described above would still be sufficient to strongly trap and retain magnetic particles. Similar calculations can be performed using different magnetic particle parameters and chip dimensions and designs. These calculations indicate that the concept of using localized magnetic fields to strongly yet reversibly trap magnetic particles is highly generalizable and may be implemented using a wide variety of designs and materials.

The trapping energy is also relevant in terms of procedures for removing the magnetic particles from the substrate. The kinetic energy $E_k$ of the bead may be computed as follows:

$$E_k = \tfrac{1}{2}(m)v^2 \tag{Eq. 4}$$

where m=mass of magnetic particle and v=velocity of magnetic particle. Thus for a particle of $m=1.5 \times 10^{-11}$ g (the approximate mass of an M-280 Dynabead) the trapping energy of the particle is equal to its kinetic energy when moving at approximately 1 m/sec. Thus if a particle were in a fluid flow at approximately 1 m/sec or greater, it would overcome the trapping energy. A corollary to this is that once trapped, a sufficiently fast fluid flow is enough to decouple the particles from their attachment sites and hence prepare the chip for reuse. For example, a fast fluid flow perpendicular to the length of the gap (i.e., a fluid flow in the y-direction on FIG. 3) and in the plane of the substrate may be used to effectively remove magnetic beads from the chip. Much slower fluid flows (e.g., on the order of less than one to several cm/sec) are used to initially assemble the array of beads on the chip and to remove excess unbound beads when the arraying is complete.

E. Extensions (1) Microfluidics

In certain embodiments of the invention a microfluidic assembly is integrated with the magnetic chip for ease of sample introduction and removal. The microfluidic assembly may be made of glass, quartz, polymers such as plastics, or any other suitable material. The microfluidic assembly includes a plurality of channels. The channels may be of any appropriate width, e.g., between 0.1 µm and 500 µm, though for some applications somewhat greater widths (e.g., in the mm range) are desirable. For many applications channel widths of between 5 and 50 µm are useful. Channel depth may fall within similar ranges. Selection of appropriate dimensions for channels may depend on the dimensions of the chip and beads to be used. The microfluidic assembly may also contain features such as wells (e.g., for holding samples, solutions, reagents), sample inlet and outlet ports, fluid valves, mixing chambers, etc.

According to certain embodiments of the invention, each array on the chip is addressed by two crossed channels. A solution containing magnetic particles is introduced with a gentle flow, e.g., via the channel that is oriented along the long axis of the magnetic islands although the other channel may also be used. The sample may be moved back and forth over the array to enhance trapping of the magnetic particles. After several seconds to minutes, a buffer flow is introduced to clear out untrapped, excess bead particles. If hybridization is to be performed on-chip, then beads with attached probes are introduced first in the above manner and then, after clearing out excess beads, the sample containing probe is introduced similarly and given time to hybridize. The hybridization process may take several hours or longer and may be performed at elevated temperature (e.g., 45 C. or higher to enhance hybridization specificity). The channels may also be used to introduce and remove reagents such as buffers, enzymes, substrates for detection, etc. Once data collection has been performed, a fast buffer flow is introduced, e.g., via the channel which is oriented perpendicular to the long axis of the magnetic islands. This aids in stripping the magnetic particles off the chip. While either channel can be used, stripping may be much more efficient when using a flow direction perpendicular to the trapping field, $H_x$. The channels can then be flushed, and the chip is ready for reuse.

Any appropriate fabrication technique may be employed to make the microfluidic assembly. The selection may depend upon the choice of materials. Appropriate techniques include various micromachining and microfabrication techniques, including film deposition processes such as spin coating, chemical vapor deposition, etching techniques, injection molding, etc. Well-known bonding methods may be used to bond a material such as glass to a substrate such as silicon. Straightforward heat bonding, which is compatible with the magnetic chip design and fabrication processes described above, may be used. Another bonding technique is anodic bonding, in which a high strength electric field is used to bond the assembly, reducing the need for high temperatures. According to this technique, a glass sheet (which can be pre-etched with the desired pattern of channels) is placed on a bare or oxidized silicon wafer, which has been patterned with magnetic regions (e.g., prepared up till Step 5 in FIG. 10). After proper alignment of the channels with the magnetic islands, the assembly is heated to approximately 350 C. while holding the substrate at a positive (anodic) potential relative to the glass. Voltages on the order of 500 V are typical, though any appropriate voltage may be used. This causes the surfaces at the interface to diffuse to form a permanent bond. After bonding, the magnetic regions are magnetized as described above. The conditions for anodic bonding are compatible with the chip fabrication processes, so modification of those processes should not be required.

As will be appreciated by one of ordinary skill in the art, numerous variations in terms of the design, materials, and fabrication technology for the microfluidic assembly may be made. In addition, devices such as pumps, tubing, heating elements, etc., may be attached to and employed in conjunction with the microfluidic assembly. Devices such as pumps (e.g., electrokinetic pumps), heating elements, etc., may be provided either on-chip or off-chip. In certain embodiments of the invention the materials used in fabrication of the microfluidic components and ancillary equipment is non-magnetic.

In general, microfluidic systems and related devices and components are well known in the art. Various aspects of these technologies are described, for example, in U.S. Pat. No. 5,603,351 and PCT US/17116 (sample cassettes); WO96/39260 (formation of fluid-tight electrical conduits); U.S. Pat. No. 5,747,169 (sealing), and WO/71243 and references therein for general description.

(2) Integrated Photodetectors

As described below, many of the schemes for detecting interactions between probes and samples and/or for encoding and decoding bead identities rely on optical detection schemes such as fluorescence detection. Thus in certain embodiments of the invention on-chip photodetectors are provided in proximity to the attachment sites for magnetic particles for detection of signals from beads, probes, and/or targets (e.g., fluorescent or luminescent signals). Photodetector technology on substrates such as silicon is well known (see, e.g., U.S. Pat. No. 5,965,452), and methods for producing integrated photodetectors (e.g., lithographic processes) are compatible with the other fabrication steps for the magnetic chip. The photodetector element (e.g., a charge-coupled device (CCD) structure, MOS photodiode, etc.) may be covered with a transparent material such as glass or plastic for protection.

Figure 12:
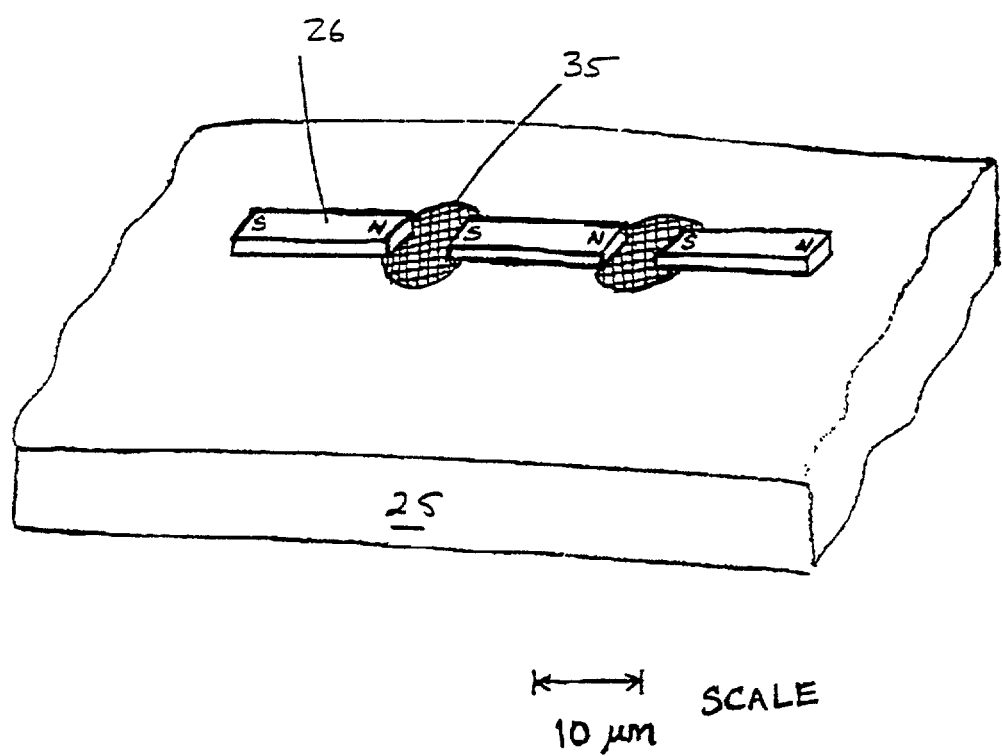
FIG. 12 shows a schematic view of a magnetic chip with integrated photodetectors on a substrate that forms the surface of the chip.

Various possibilities exist for integrating photodetectors into the magnetic chip of the invention. In one embodiment, referring to FIG. 12, integrated photodetectors 35 can be built on a silicon substrate 25 that forms the surface of the chip. Magnetic regions may be formed prior to formation of the photodetectors. Alternatively, the photodetectors may be formed first, and the magnetic regions formed afterwards. The photodetectors can be distributed in a regular pattern that substantially corresponds to the pattern of gaps between magnetic regions, and can be substantially equal in number to the number of magnetic regions. Circuitry (not shown) coupled to the photodetectors can transmit the fluorescent signals to a processor which can process the signals into an image-map which can be analyzed.

Including optical detection capabilities on the chip itself offers a number of advantages. Due to the proximity of the on-chip photodetectors to the arrayed beads, the sensitivity of this detection scheme will likely be significantly superior to confocal scanning. This may be important when detecting genomic targets under conditions in which relatively few target molecules are present, which is likely to be an increasingly important future direction for high-density array technologies. Photodetector integration onto the chip will further enhance the photon capture efficiency. The reusability of the chip over multiple arraying runs may make on-chip detection an economically feasible approach. On-chip detection enhances the portability of the system since proximity to fixed detection devices is not necessary. In addition, on-chip detection may be particularly useful when the chip is packaged in a housing, as is the case in certain embodiments of the invention.

III. Magnetic Particles

As will be evident, the magnetic particles to be coupled to the magnetic chip may be in any suitable form, including beads. For descriptive purposes the magnetic particles will be referred to herein as beads or magnetic beads, without thereby imposing any limitation on the size or shape of the particles. The beads may have any suitable size, depending upon the characteristics of the chip on which they are to be dispersed. In certain embodiments of the invention the beads are substantially spherical. For example, spherical beads with a diameter between about 1 and 10 microns may be used. In certain embodiments of the invention spherical beads with diameter between about 1 and 5 microns may be used. In certain embodiments of the invention spherical beads with a diameter between about 1 and 3 microns may be used. In addition, nanoparticles such as nanospheres may be used. The manufacturing technologies described above are compatible with fabrication of arrays with feature sizes down to the submicron scale, thus they can readily be employed to fabricate chips for use with nanoparticles.

As will be evident, the size of the particles influences a number of parameters resulting in various tradeoffs. For example, if smaller particles are used the maximum achievable array density is correspondingly greater. However, the larger surface area of a bead with a greater diameter allows the attachment of more probes per bead, resulting in a greater sensitivity and potentially a greater signal intensity for each bead and may also allow greater encoding flexibility.

The beads may comprise any appropriate magnetic material, e.g., iron (Fe), cobalt (Co), or nickel-iron alloys. As used herein, the term magnetic material includes paramagnetic materials. The beads may comprise nonmagnetic materials such as polystyrene in which magnetic subparticles (e.g., $Fe_3O_4$ particles) are embedded. Such particles may, for example, be dispersed throughout the nonmagnetic material or may form a core or shell below the surface of the nonmagnetic material. For biological applications, preferably at least the surface of the bead is made of a biocompatible material. Nonmagnetic biocompatible materials that may be used to coat the surface of a nonbiocompatible material such as iron include polymeric materials such as polystyrene, latex, and numerous other materials well known in the art.

In certain embodiments of the invention paramagnetic beads are used. Paramagnetic materials magnetize only when an external magnetic field is present, and thus paramagnetic beads exhibit minimal clumping. Biocompatible paramagnetic beads are available from a number of manufacturers (e.g., Dynal, Bangs Labs, Spherotech). Such beads are widely used for a variety of biological applications, and protocols for coupling biological molecules such as nucleic acids and proteins are well established. In addition, paramagnetic beads that are pre-conjugated with various binding ligands are available. For example, superparamagnetic beads manufactured by Dynal, Inc., with a 2.8 micron diameter, have been used in conjunction with a magnetic chip of the invention as described in more detail in Examples 2, 3, and 4.

Superparamagnetic beads have a proven record of more than 15 years in commercial use. Such beads are manufactured by dispersing ferrite crystals throughout a polystyrene bead during its polymerization. The crystals are ferromagnetic, but because of their nanoscale size they behave not ferromagnetically but paramanetically (the phenomenon has been termed superparamagnetism). It is believed that the orientational crystals are so small that they are randomized by thermal effects at room temperature. An array of such particles has essentially no renamence; it magnetizes substantially linearly in an applied magnetic field, losing essentially all magnetism when the external field is removed. This feature results in minimal clumping. The beads may be encapsulated for efficacy when used with enzymes (e.g., to avoid contact with iron-containing molecules) and the surface is easily modified to covalently attach biomolecules such as nucleic acids or proteins or small organic molecules.

A bead may include a detectable material such as a dye, a colorant, or a hybridization tag so that the bead may be detected on the array and identified among other beads. The detectable material can be incorporated within the bead, can be present on the surface, and/or can be linked to the bead. A particular detectable material or combination thereof can correspond to a particular probe that is attached to the bead, so that identification of the detectable material will also identify the probe. In certain embodiments of the invention a particular detectable material can correspond to a particular target, so that identification of the detectable material will also identify a target that interacts with the probe.

The range of commercially available beads (both magnetic and nonmagnetic) is vast. Beads made of many different materials and sizes are available. Beads incorporating various molecules such as fluorescent dyes, beads conjugated with various moieties or having surfaces modified to facilitate such conjugation are available. See, for example, the Microsphere Selection Guide from Bangs Laboratories, Inc., 9025 Technology Drive, Fishers, Ind. 46038-2886 at http://www.bangslabs.com/products/bangs/guide.php and additional documentation available at the Bangs Laboratories Web site (http://www.bangslabs.com).

IV. Assembling and Disassembling Arrays

A. Assembling an Array of Magnetic Particles

The magnetic particles may be introduced to the surface of the magnetic chip according to any appropriate technique. In general, it may be desirable to dispense the beads in a solution prior to introducing them to the chip. A gentle fluid flow is an appropriate means of introducing the beads to the surface of the chip. Multiple populations of beads can be combined into a single solution prior to dispensing, or individual populations of beads can be sequentially dispensed. The beads can be introduced to the chip by pouring the solution onto the chip either directly or through a device such as a tube or funnel. The beads can also be dispensed onto the chip using a syringe, pipette, etc. In those embodiments of the invention in which a microfluidic assembly is incorporated, the beads may be introduced to the surface of the chip using the channels of the assembly, possibly with the assistance of a pump.

The beads can be introduced at any appropriate concentration and in any convenient volume of fluid. The concentration may be varied depending upon, e.g., the size of the beads, the properties of the fluid in which they are dispensed, the number of attachment locations on the chip, etc. According to certain embodiments of the invention an appropriate concentration may range from approximately 50,000 to 100,000 beads/μl, from approximately 20,000 to 50,000 beads/μl, from approximately 15,000 to 20,000 beads/μl, from approximately 10,000 to 15,000 beads/ml, from approximately 5,000 to 10,000 beads/μl, etc. Higher concentrations, e.g., up to 150,000, 200,000 or even more beads/μl may be used.

The total number of beads to be introduced may be varied according, for example, to the number of attachment sites on the chip. The ratio of beads to attachment sites may influence the arraying behavior of the beads. For example, if there are many more attachments sites than beads, it is likely that most attachment sites will be empty while those that are occupied are occupied by only a single bead. On the other hand, if there are many more beads than attachment sites, most sites will be occupied by at least one bead. While not wishing to be bound by an theory, in general, the occupation of identical domains on the chip is governed by Poisson statistics, which can be used to predict the likelihood that a domain will be occupied by 0, 1, or more beads. One of ordinary skill in the art will be able to select an appropriate number of beads to dispense. As discussed above, the trapping of beads on the chip can be optimized by appropriate selection of chip geometry and size of the magnetic domains. For example, too small a gap between magnetic domains will prevent bead trapping in the center of a gap while too large a gap instead allows trapping of multiple beads on the edges of the magnetic domains. This effect is demonstrated in Example 2.

Once the beads have been dispensed on the chip, they can be trapped by the localized magnetic fields created by the magnetic domains. This process may take from seconds to minutes. Trapping may be aided by gently moving or agitating the chip to allow an even dispersal of beads across the chip. A low surface tension liquid medium may be used to facilitate dispersal of the beads. A surfactant (e.g., a detergent such as SDS or Tween®) may be included in the bead solution to help in spreading the beads over the chip by reducing the hydrophobic interactions of the beads with the chip surface and the surface tension interactions with the drop surface. For example, diluting beads in 1X TE (Tris-EDTA) with 0.1% SDS maybe appropriate. Concentrations of SDS tenfold higher or lower may also be used. However, when reactions (e.g., hybridization or enzymatic reactions) are performed prior to introducing the beads to the chip surface, care must be taken to ensure that the detergent concentrations do not interfere with such reactions. When reactions are to be performed on-chip (i.e., after bead trapping), the chip can be washed sufficiently to remove detergents prior to introduction of sample, reagents, etc.

As described in Examples 2 and 3, the arraying behavior of the beads may be examined experimentally, e.g., by using fluorescently labeled beads and obtaining a laser fluorescence scan of the chip surface after allowing the beads to attach. Alternatively, an optical microscope can be used (e.g., with unlabeled beads) to observe their arraying behavior. Laser scanning may be preferable, however, because it readily allows quantification of signal to noise ratio.

Once the beads have been captured the remaining solution (containing uncaptured or weakly attracted beads that may cluster at the edges of an occupied gap region) can be removed, e.g., using a gentle fluid flow. The beads and/or associated probes or targets can then be detected as described below. Alternately, samples or other reagents may be introduced to the chip and reactions or assays performed prior to detection.

B. Disassembling an Array of Magnetic Particles

After detection is complete, magnetic particles can be removed from the surface of the chip, e.g., by applying a rapid fluid flow over the chip sufficient to overcome the trapping energy. (Trapping energy for magnetic beads is discussed above.) For example, a fluid flow of approximately 1 m/sec is sufficient to overcome the trapping energy of 2.8 μm M-280 Dynabeads. The fluid flow for removing the beads can be applied according to any of the procedures used for introducing the beads to the chip surface.

Another approach is to remove beads by applying an alternating magnetic field (e.g., with a small electromagnet and AC current) while flowing a solution such as wash buffer over the chip. The average magnetization would then be zero, and particles could therefore be removed by a gentle fluid flow (e.g., in the cm/sec range). The magnetic regions would then be remagnetized, e.g., using DC current. However, since this approach would require chip magnetization/demagnetization between runs it may be less convenient than simply using fluid to remove the beads.

V. Encoding and Decoding

For arrays in which probe is bound to substrate (e.g., conventional oligonucleotide arrays), the identity of each probe is positionally encoded, i.e., the identity of a probe may be ascertained based on the position of the probe on the substrate. This is not the case, however, for random order arrays such as those of the invention. Therefore, in many situations (e.g., most situations involving multiple different probes) a method for determining the identity of the probe and/or target is needed. In some instances determining the identity of a probe or target can be performed directly (e.g., by sequencing a nucleic acid probe or target). However, typically the identity of the bead and/or probe is encoded prior to performing an assay in order to facilitate subsequent determination of the identity of the probe (decoding).

Any of a variety of methods well known in the art may be used for encoding and decoding beads, probes, and/or targets. These methods may also, in general, be used in combination, e.g., to increase the number of possible encodings. Encoding typically involves imparting some sort of detectable property to the bead, probe, and/or target to be encoded, wherein the nature or value of the detectable property differs between different populations of beads, probes, and/or targets. The nature or value of the detectable property corresponds to the identity of the bead, probe, and/or target, so that determining or measuring the detectable property provides information as to the identity of the bead, probe, and/or target. The descriptions of encoding and decoding techniques provided herein are intended to be exemplary and are not to be considered as limiting the invention in any way. These methods and others are all well known in the art, and methods not described herein can also be used with the invention. Various encoding and decoding strategies are described in, for example, Wo9967641, WO0048000, WO0071995, and WO0075373.

Typically the purpose of encoding beads or probes is to allow the mixing of populations of beads (where each population of beads bears a different attached probe or probes) prior to performing an assay in which the mixed population of beads is exposed to target. After performing the assay the identity of probes (either all probes or only those that interacted with target) can be determined by decoding. In general, if the probes themselves are encoded the beads need not be encoded (although they may be). When the probes themselves are not encoded (or when it is desired to use a different encoding/decoding scheme from that employed in encoding the probes), the beads may be encoded. The encoding of a bead then serves to identify the attached probe.

In general, a bead encoding strategy may be implemented in any of at least four different ways (and combinations thereof may also be used). Magnetic beads can be "color-coded" by providing them with one or more optically detectable moieties (e.g., fluorescent dyes). The detectable moiety may be provided by impregnating or coating the bead, or conjugating the moiety (either directly or indirectly) to the surface of the bead. The encoding can take place during or after manufacture of the bead. For convenience, optically detectable moieties will be referred to herein as dyes, without intending any limitation thereby. The identity of the dyes may be varied, and beads may incorporate multiple different dyes. The concentration(s) of the dye(s) may also be varied, resulting in different intensity levels. For example, with three colors provided at 10 different concentrations (intensity levels), 1000 different combinations are obtained. Using this scheme it is possible to encode and subsequently identify 1000 different populations of beads (e.g., beads to which any of 1000 different probes are attached). Numerous suitable dyes are known in the art, and beads incorporating such dyes are commercially available. Fluorescent or luminescent labels that can be used include, but are not limited to, fluorescent lanthanide complexes, including those of europium and terbium, fluorescein, rhodamine, tetramethylrhodamine, eosin, erythrosin, coumarin, methyl-coumarins, pyrene, malachite green, stilbene, Lucifer Yellow, Cascade Blue, Texas Red, FITC, Cy3, Cy5, etc. Such labels and others are described in Mason, W. (ed.) and Mason, B., Fluorescent and Luminescent Probes, Academic Press: San Diego, 1999, in *Handbook of Fluorescent Probes and Research Products* (8th Ed.), Molecular Probes, Inc., and at http://www.probes.com. In addition to the afore-mentioned molecules, fluorescent nanocrystals referred to as quantum dots may be used to encode the beads. Fluorescent quantum dots consist of a core of a cadmium selenide (CdSe) nanocrystal ranging in diameter from approximately 18 Å to 70 Å, which may be wrapped in a shell of zinc sulfide. The use of quantum dots to label and distinguish between populations of microbeads is described in Han, M., et al., "Quantum-dot-tagged microbeads for multiplexed optical coding of biomolecules", *Nat. Biotechnol.*, 19:631-635, 2001. When multiple dyes or other fluorescent, luminescent, or otherwise optically detectable moieties are used, it is important to ensure that they are distinguishable, e.g., that they absorb and/or emit light at sufficiently different wavelengths to be distinguishable by the detection means employed.

A second strategy for encoding and decoding is to use a set of hybridization tags. These tags are nucleic acid molecules (encoding tags) whose identity can be determined by hybridization to nucleic acid molecules (decoding tags) having a substantially complementary sequence. By attaching one or more hybridization tags to a particular population of beads (i.e., a population of beads bearing a particular probe), the identity of the bead can be determined by performing hybridization using the decoding tags, which are typically labeled (e.g., with a fluorescent dye) to allow their subsequent detection. As an example, with six different hybridization tags one can obtain 1+6+15+20+15+6+1=64 different combinations and thus encode 64 different populations of beads (assuming between 0 and 6 different hybridization tags are assigned to each bead population). Hybridization tags may range in length from several nucleotides to 50 or more. Tags ranging from approximately 10 to approximately 25 nucleotides in length may be particularly appropriate. It will be appreciated that a greater number of nucleotides allows for more different populations of beads to be encoded but adds to the complexity of synthesis. Methods for attaching nucleic acids to beads are well known in the art and are discussed further in the Assays section below.

In a typical experiment groups of beads are prepared and various combinations of hybridization tags and probes are bound to the beads in each group. Then a pool of beads is formed, containing a mixture of the various populations. The sample to be interrogated can then be hybridized to the beads in solution or after arraying on the chip. Decoding is performed by adding complements of the six hybridization tags (i.e., the decoding tags) while the beads remain trapped on the chip. This can be done serially, with detection after each hybridization. A more efficient approach is to perform the hybridization in one step, i.e., using a mixture of decoding tags with a different dye attached to each different decoding tag. In this case, the combination of colors reveals the identity of the bead by decoding the combination of tags it contains. The target(s) in the sample are labeled using a different method or a different dye to that used to label the decoding tags. Interaction of a probe with a target (e.g., hybridization of a DNA probe to a complementary nucleic acid in the sample) is revealed by detecting the label specific to target.

Instead of, or in addition to, employing hybridization as a method of decoding nucleic acid tags, direct sequencing of the tags or probes attached to a bead may be performed. For instance, one can decode the tag or probe sequence on the bead and consequently the bead by sequencing the tag or probe on the bead to reveal the identity of the tag or probe. By directly sequencing the probe the need for employing encoding scheme is avoided because the sequence itself reveals the identity of the probe. With mini-sequencing, the particles do not have to be pre-labeled with a detectable material for decoding. Using mini-sequencing, for example, the DNA sequence surrounding a polymorphism provides the ability to identify the DNA fragment.

Any appropriate method of on-bead sequencing may be used. One such method is pyrosequencing. In a typical pyrosequencing process, complementary nucleotides are sequentially added to a single-stranded DNA. With each addition, pyrophosphate is released in an amount which is characteristic of the nucleotide being added. ATP sulfurylase quantitatively converts pyrophosphate to ATP in the presence of adenosine 5' phosphosulfate. This ATP drives a luciferase mediated conversion of luciferin to oxyluciferin that generates visible light in amounts that are proportional to the amount of ATP. The light produced in the luciferase-catalyzed reaction can be detected by a detection device such as a charge coupled device or the above-described photodetectors. Various other enzymatic methods are known. Pyrosequencing technologies are described in greater detail at "http:/www-.pyrosequencing.com/documents/about/tech.html" and in Ronaghi, et al., *Science,* 281:363, 1998.

Conservative calculations and also, experiments indicate that a template density of 1000 molecules/$\mu m^2$ will yield enough pyrosequencing photons to give a signal to noise greater than 10:1 with a cooled, high-efficiency, unamplified CCD camera. The magnetic beads can easily be coupled to DNA probes at an effective density of 10,000 molecules/$\mu m^2$ on each bead. This should easily be detectable with a standard CCD setup.

A fourth strategy for encoding and decoding bead identities is to use an intrinsic property of the magnetic beads such as their magnetization. The magnetic bead particles may be encoded with a varying magnetization (magnetite content) and detected via their differential response in a magnetic field. Spin valve detectors (explained below in the section entitled Detection) may be used to detect such magnetic beads and differentiate between populations of beads having different magnetization. Other detection methods may also be used.

The primary purpose of encoding a bead is to allow the identity of a probe attached to the bead to be subsequently determined. A similar result may be obtained by applying an encoding scheme to the probe itself instead of, or in addition to, encoding the bead. Many of the above encoding approaches may be applied to probes. For example, a probe can be color-coded, e.g., by attaching a fluorescent dye molecule or incorporating such molecules during synthesis of the probe. Labeled nucleic acid probes may conveniently be obtained by using one or more fluorescently labeled nucleotides in the synthesis procedure. One or more hybridization tags may be attached to or included in a probe. For example, where the probe is a DNA molecule, the probe may contain a portion that is substantially complementary to a target sequence and another portion that is substantially complementary to one or more decoding tags. As mentioned above, direct (on-bead) sequencing of a probe can also be used to identify the probe.

The field of combinatorial chemistry frequently involves synthesis of molecules on beads using a stepwise approach (e.g., split and pool synthesis). These methods may involve the use of encoding in order to allow a subsequent identification of the structure of the synthesized molecule. Similar encoding schemes may be used in the context of the present invention, particularly in situations where a probe is synthesized on the bead. Such encoding schemes are described, for example, in WO 98/53093 and references therein; Barnes, C. and Balasubramanian, S., Czarnik, A. W., "Recent developments in the encoding and deconvolution of combinatorial libraries", *Curr Opin Chem Biol.* (2000) Jun;4(3):346-50; Czarnik, "Encoding methods for combinatorial chemistry", *Curr Opin Chem Biol.* (1997) Jun;1(1):60-6; and Maclean, D. et al., "Encoded combinatorial chemistry: synthesis and screening of a library of highly functionalized pyrrolidines" *Proc Natl Acad Sci USA.* 1997 Apr 1;94(7):2805-10.

In general, in the schemes described above encoding of either the bead or the probe is sufficient to identify the bead (and thus the attached probe) or to identify the probe respectively. Thus if the bead is encoded no modification to the probe for encoding purposes is required. Conversely, if the probe is encoded, no independent encoding scheme for the bead is required, and the probe may be attached to an unmodified magnetic bead. An advantageous use of hybridization tags that may be used for assays involving nucleic acid hybridization (e.g., genotyping assays) involves modifications to both the bead and the probe.

According to this hybridization tag scheme populations of beads are encoded using any of the strategies described above (e.g., color-coding, magnetization, hybridization tags). A set of standard hybridization tags (e.g., oligos of 20 nucleotides in length) is selected to encode the probes. If hybridization tags are also used to encode the beads, a different standard set of hybridization tags should be used to encode the probes. The number of different tags can be arbitrarily large, depending on the number of different probes that are to be employed in the assay. The tags can be selected to interact (i.e., hybridize) minimally with each other and can be balanced with respect to properties such as melting temperature.

Probes whose sequence includes both (1) a sequence that is complementary to the sequence of a target to be detected by that probe and (2) the sequence of a hybridization tag assigned to that probe are prepared. Such probes may be, for example, approximately 40 nucleotides in length, where one 20 nucleotide stretch is a particular hybridization tag while a second 20 nucleotide stretch is intended to interrogate the sample (i.e., it is complementary to a target sequence of interest). The probes may also incorporate a linker sequence at the end to be attached to the bead. An oligo having a sequence complementary to one of the hybridization tags is coupled to an encoded population of beads. The probe having the complementary hybridization tag is then combined with that population of beads, and hybridization is allowed to occur between the bead-linked oligo and the complementary portion of the probe (the hybridization tag).

Beads (with associated probes attached by hybridization via the hybridization tag) from multiple populations are pooled prior to interrogation of the sample. Targets within the sample are labeled, e.g., with a fluorescent molecule different to any such molecule used to encode the beads. Hybridization between sample and probe is allowed to occur either prior to assembling the bead array or on-chip. After assembly of the array (and hybridization, if hybridization is performed on-chip), detection is performed. Following detection, decoding involves determining the identity of any beads with which the target has interacted (e.g., beads that have a target bound to their coupled probe). The bead is decoded using the decoding strategy appropriate to the way the bead was encoded. Decoding the identity of the bead reveals the identity of the hybridization tag whose complement was coupled to the bead. The identity of this hybridization tag in turn reveals the identity of the probe, including the identity of the sequence that was included in the probe in order to interrogate the sample. Thus the fact that the target interacted with (e.g., bound to) a particular probe is revealed.

In the context of a genotyping assay, this approach allows reformatting of the variable sequence of interest at the genomic region of interest to a standard hybridization tag. The power of this technique is that one can always use a pre-selected set of 20-mer hybridization tags with exceptional hybridization properties (e.g. no cross-interactions between them). The same bead populations are therefore usable experiment after experiment with an arbitrary choice of markers (sites) that one wishes to interrogate in the genome. All that is required is the synthesis of probes that include the complement of the marker and a hybridization tag whose complement is attached to a population of beads.

The foregoing approach is applicable to contexts other than genotyping and to biomolecules other than DNA. For example, RNA samples can be reformatted similarly. In addition, proteins can be reformatted with the same set of pre-selected 20-mer tags (e.g., using unique aptamers that bind to a specific protein). Nucleic acid aptamers capable of binding to virtually any protein of interest can be developed. See, for example, U.S. Pat. Nos. 5,270,163; 5,475,096; 5,567,588; 5,595,877; 5,637,459; 5,683,867, 5,705,337 and related patents. Reformatting approaches have the benefit of allowing different upstream assays on different target samples to be interrogated by the same chip hybridization platform. By decoupling the upstream biochemistry from the downstream detection process and executing the whole protocol for hundreds or thousands of probes in parallel, provides a very powerful analytic platform. The strategy of reformatting using hybridization tags, software used to generate the tags (publicly available), and genotyping assays using this approach is described in Hirschhorn, J., et al., "SBE-TAGS: An array-based method for efficient single-nucleotide polymorphism genotyping", *Proc. Natl. Acad. Sci.,* 97(22): 12164-12169, 2000 and in Fan, et al., "Parallel genotyping of human SNPs using generic high-density oligonucleotide tag arrays", Genome Res. 2000 Jun;10(6):853-60. A set of standard hybridization tags is available at http://waldo.wi.mit.edu/publications/SBE-TAGS/.

VI. Assays

The magnetic chip and bead technology can support any of a wide variety of reactions and assays. These reactions and assays may include essentially any of the reactions and assays conventionally performed using molecules attached to beads and those performed using conventional DNA arrays. For example, nucleic acid hybridization assays, enzymatic reactions, antigen-antibody reactions, assays for protein-protein interactions, assays for interaction of small molecules with nucleic acids and/or proteins, screening of combinatorial chemical libraries, etc., can all be performed using bead-based approaches.

The magnetic chip of the present invention may find particular use in reactions involving nucleic acids and in assays for detecting nucleic acid interactions. A large and varied assortment of such reactions and assays are available, a number of which are described, for example, in WO0048000 and in WO0063437 and in patents and publications referenced therein. Reactions include various ligation and polymerization reactions including amplification reactions such as polymerase chain reaction (PCR), oligonucleotide ligase amplification (OLA), cycling probe technology (CPT), strand displacement assay (SDA), transcription mediated amplification (TDA), nucleic acid sequence based amplification (NASBA), rolling circle amplification (RCA), and invasive cleavage technology. Assays include, but are not limited to, genotyping assays such as simple or competitive hybridization, allelic PCR, OLA which may employ a ligation chain reaction (LCR), single base extension (SBE), allele-specific primer extension (ASPE), exonuclease assays such as Taqman, invasive cleavage, and/or a combination of any of the foregoing. Additional examples of assays that can be performed in the context of the present invention are found in, Steemers, F., et al., "Screening unlabeled DNA targets with randomly ordered fiber-optic gene arrays", *Nat Biotechnology,* 18:91-94, 2000, describing use of bead-coupled probes incorporating molecular beacons for detection of mutations in genes of the cystic fibrosis transmembrane conductor region.

Example 3 describes a DNA hybridization assay in which oligonucleotides were attached to magnetic beads (via streptavidin-biotin linkage), which were then incubated with complementary oligonucleotides labeled with the fluorescent molecule Cy3. FIG. 13 shows a fluorescence image obtained after performing the hybridization off-chip and then arraying the beads on a magnetic chip of the invention.

Assays involving RNA, e.g., measurements of mRNA abundance may conveniently be performed using the magnetic chip, as is commonly done using conventional cDNA or oligonucleotide arrays. Another example of an assay involving RNA that can be performed in the context of the present invention is described in Brenner, S., et al., "Gene expression analysis by massively parallel signature sequencing (MPSS) on microbead arrays", *Nat Biotechnol,* Jun;18(6):630-4, 2000, describing a method for determining mRNA abundance using cDNA libraries cloned onto the surfaces of microbeads.

The magnetic chip may also be used to form randomly ordered protein arrays, e.g., antibody arrays. The use of antibody arrays is described, for example, in Haab, B., et al., "Protein microarrays for highly parallel detection and quantitation of specific proteins and antibodies in complex solutions", *Genome Biol.* 2001;2(2), 2001. Other types of protein arrays are known in the art. Antibody-based assays such as enzyme-linked immunosorbent assays (ELISA) may also be performed on beads and thus employed in the context of the present invention.

In order to perform many of the above assays it is necessary to couple one or more molecules to a magnetic particle. Any of a wide variety of coupling methods may be employed. Coupling can be covalent or noncovalent. One of ordinary skill in the art will readily be able to select and apply an appropriate method (e.g., depending upon the type of molecule to be coupled). Coupling can be performed using chemical or affinity capture, cross-linking, electrostatic attachment, etc. In affinity capture, the bead is derivatized with one member of a binding pair while the molecule to be captured is derivatized with the other. Appropriate binding pairs include, but are not limited to, (i) biotin and streptavidin or derivatives thereof; (ii) complementary or substantially complementary nucleic acids (e.g., oligo-dT and poly-A regions of mRNA); (iii) protein A, G, or L and Ig; (iv) carbohydrate-lectin pairs; (v) hapten-antibody pairs, (vi) amineal-dehyde pairs, etc. Molecules may be attached to beads via linkers, of which a large number are known in the art. See, for example, Pierce Chemical Co. Catalog, Pierce Chemical Co., Rockford Ill. See also, Hermanson, G., *Bioconjugate Techniques*, Academic Press, San Diego, 1996. Examples of linkers include sulfhydryl reactive linkers such as maleimides, etc. The surface of beads may be derivatized with various functional groups to facilitate attachment of molecules. Such functional groups include amino groups, carboxyl groups, aldehydes, amides, chloromethyl groups, hydrazides, hydroxyl groups, and sulfonates. Methods for attaching nucleotides and/or nucleic acids to the surfaces of derivatized microbeads, e.g., via a base-labile group, and methods for attaching polypeptides, e.g., via amino groups are also well known in the art. Molecules such as nucleic acids or polypeptides may also be synthesized directly on the bead.

As noted above, performing assays on microbeads has a number of advantages. For example, in multistep assays it is convenient to add and remove reagents when probes are bound to beads. Using the magnetic chip of the present invention it is possible to perform one or more steps of a multistep assay prior to dispersing the beads on the chip surface, while other steps may be performed after dispersal. This possibility enhances the flexibility of the system. For example, one could perform a series of hybridizations under different conditions (e.g., different temperatures), assemble a random array of beads, and then perform additional steps (e.g., enzymatic reactions such as ligation and then detection) under uniform conditions.

VII. Detection

Numerous detection methods are known in the art and are suitable for detecting beads, probes, targets, and the interaction between probes and targets. In general, an appropriate detection scheme will depend upon the method used to encode or label the beads, probes, and/or targets. For example, where a labeling or encoding scheme employs optically detectable moieties, e.g., fluorescent dyes, confocal scanning or CCD detection may be appropriate. If oligonucleotide tags are employed direct sequencing, as described above, may be used. Various detection methods that are useful in the context of the invention are described below. These methods are, in general, known in the art and the descriptions provided below are not intended to be limiting in any way. Different embodiments of the invention may employ different detection techniques or combinations thereof.

A. Confocal Scanning

This method is now in standard use to perform fluorescence scans of microarrays. After forming a random order array on the magnetic chip, the chip is inserted into a commercially available fluorescence scanner for data collection. As mentioned above, a density of 10,000 oligonucleotide probes/mm$^2$ surface area is readily achievable. Typically, a 2.8 µm diameter bead may contain about 100,000 molecules that are covalently bound to the surface. Assuming a worst case hybridization and signal collection efficiency of only 1%, this results in approximately 1000 fluors/bead. Detection thresholds for most commercial scanners are close to one fluor/bead, yielding three orders of magnitude in the signal dynamic range for each site (bead) on the array.

B. CCD Detection

This detection scheme is an alternative to confocal scanning. Advantages include continuous data collection over the entire chip. When using a method such as pyrosequencing to decode the beads, CCD detection may be the method of choice although signal to noise ratios may be slightly better with confocal scanning.

C. Direct Sequencing

On-bead sequencing of tags and/or probes is discussed above.

D. Integrated Photodetectors

Fabrication and use of on-chip photodetectors is discussed above.

E. Detecting Beads Having Varying Magnetization

As discussed above, an encoding/decoding scheme for magnetic beads may involve detecting differences between populations of beads having different magnetization. Magnetic fields (and hence the magnetic particles) are detectable with spin valve technology. This technology is at the core of the multi-billion dollar computer hard-drive industry. Briefly, the spin valve sensors consist of materials whose resistance changes in response to a magnetic field. Thus, by passing a current through a strip of such material and measuring the resistance, once can detect the local magnetic field. Data is read from a spinning hard drive by such sensors. Advances in such materials (Giant MagnetoResistive—GMR) have enabled the fabrication of micron-scale sensors with very high magnetic field detection sensitivities. This technology has been applied to detect magnetic bead particles by hybridization of the bead particles to an array of fabricated sensors as described, for example, in R. L. Edelstein, et al., "The BARC biosensor applied to the detection of biological warfare agents", *Biosensors and Bioelectronics*, 14 (2000) pp. 805 813 (See also WO0061720). As described therein, the presence or absence of a magnetic bead above a fabricated spin valve is detected by attachment of the bead to the surface above the valve. In our setup, we would use the magnetic bead chip to form arrays of such beads, and use the spin valve read-head to scan the magnetic fields (and encoding) of the various beads by the response. In the context of the present invention, a similar detection scheme could use a single read head (spin valve) which would scan the magnetic chip for magnetic fields and variation on the fields. Great sensitivity can be obtained using schemes such as lock-in detection. The chip may also be slowly spun in a configuration like a hard drive to leverage this highly developed technology.

Other embodiments of the invention will be apparent to those skilled in the art from a consideration of the specification or practice of the invention disclosed herein. It is intended that the specification and examples be considered as exemplary only, with the true scope and spirit of the invention being indicated by the claims that follow the Examples.

EXAMPLES

Example 1

Fabricating Magnetic Chips (1) Cobalt film approximately 700-1000 nm thick was deposited on a silicon wafer with a diameter of approximately 3.0 inches. The cobalt layers were sputtered sequentially without breaking vacuum using a UHV DC magnetron sputtering system at 2×10⁻⁸ torr. The deposition rate was 0.39 nm/sec. An e-beam lithographic pattern was written using a Hitachi HL-700F instrument, a direct write patterning tool with a minimum feature size of 50 nm, and a UVN30 photoresist at 5.5 Krpm spin for 40 sec. The resulting photoresist layer was approximately 500 nm thick. The photoresist was then developed with MF-CD 26 for 30 sec. The chip configuration defined by the mask resulted in a pattern of diamond-shaped magnetic regions.

To fabricate the magnetic islands, argon sputter etching was performed in an ion-milling etcher without breaking vacuum and with the photoresist as the mask. Time intervals of 10 min etching/10 min cooling were used for a total of 80 min. The remaining photoresist was stripped using a 1165PR stripper with an ultrasonic vibrator for approximately 100 min at 95° C. Finally, the magnetic islands were magnetized along the x-axis using a vibration sample magnetometer (VSM) at 9000 Gauss to ensure saturation of the magnetic islands.

(2) A chip was fabricated on a wafer of silicon essentially as described above except that optical lithography was used rather than e-beam lithography, using visible light to form the mask patterns. An image of the entire wafer (magnetic chip) is shown in FIG. 9. The wafer contains an array of arrays at a spacing of approximately 0.1 inch in each direction. Each spot which is visible is itself a microarray of magnetic islands (shown at greater magnification in FIGS. 6 and 11) in a 30×30 configuration, with an island-to-island spacing of approximately 30 µm in both the x and y directions. The wafer therefore contains approximately 900 sites per subarray and well over 500 such subarrays. An experiment involving the analysis of 100 genomic markers on each of 500 individuals could be performed in one run on this wafer (assuming 9-fold redundancy).

Example 2

Assembling a Random Array of Magnetic Beads on a Magnetic Chip

A magnetic chip was fabricated essentially as described in Example 1 except that (i) the mask was designed to produce a chip with a 10×10 array of arrays, with each subarray having a 30×30 configuration of magnetic islands; (ii) the magnetic islands were diamond-shaped rather than rectangular and had an island-to-island spacing of approximately 20 µm in both the x- and y-dimensions, and (ii) the etching time was varied across the chip in the x-dimension, resulting in a gap of variable width, ranging between 1 and 4 µm.

A stock solution of superparamagnetic beads (streptavidin-conjugated M-280 Dynabeads obtained from Dynal Biotech, Inc.) was washed with buffer according to the directions of the manufacturer and labeled with biotinylated fluorescent R-phycoerythrin dye (Molecular Probes, Inc.) also according to the directions of the manufacturer. The beads were diluted at 40:1 in 1×TE (Tris-EDTA) with 0.1% SDS, yielding a concentration of approximately 17,000 beads/µl. A 10 µl drop of the labeled bead solution was applied to the magnetic chip with a Pasteur pipette, and the beads were allowed to become trapped by the localized magnetic fields at room temperature for approximately 5-10 minutes. The remaining solution was drained off the chip. The chip was then scanned for fluorescence in a confocal array laser scanner (excitation at 488 nm, fluorescence at 570 nm) to visualize the beads on the array. A fast fluid flow (1 m/sec was used to remove the beads from the chip after detection.

FIG. 8 shows the laser-induced 570 nm fluorescence scan of the entire chip with a random array generated as described above. The overall pattern of the 10×10 array of arrays is clearly visible. The inset shows an enlarged view of one of these subarrays, containing a 30×30 pattern of magnetic regions. The vertical scale in the image is 20 µm/count. Thus the inset shows a section of the chip 70 counts=1400 µm in length. The arraying of the magnetic beads in a grid-like pattern is clearly visible. The current resolution is 10 mm per pixel in the vertical direction. Since the magnetic regions are spaced 20 mm apart, bead trapping can be seen on every other line. (The very faint spots next to bright ones in the image are an artifact of the overall resolution of the laser scanner. A factor of two improvement in the resolution would eliminate this artifact.)

The effect of gap width on the arraying behavior of the magnetic beads is clearly visible in FIG. 8. The right side of the figure shows subarrays having a gap width of approximately 1 mm, which resulted in a low trapping efficiency. The trapping efficiency increased as the gap width increased (from right to left across the image). The maximum trapping efficiency occurred at a gap width approximately the same as the diameter of the beads (3 µm). A lower trapping efficiency was observed with a gap width greater than the bead diameter (left side of image). In addition, the increased gap width resulted in trapping of multiple beads at some locations.

Example 3

Detecting DNA Hybridization Using a Random Array of Magnetic Beads

A stock solution of superparamagnetic streptavidin-conjugated M-280 Dynal beads (10 mg/ml) was cleaned thrice following the manufacturer's directions. The stock beads are specified to bind up to 20 pmole of biotinylated oligo per 10 ul of stock beads. We cleaned 10 ul of stock beads and diluted them 2-fold to 20 ul. 200 pm of biotinylated oligo (2 ul of 100 pm/ul) was then added and bound to the bead for 30 minutes at 40° C. while shaking on an Eppendorf Thermomixer. 1M NaCl salt buffer conditions were used, in accordance to the manufacturer's protocols. A ten fold excess of biotinylated oligo was used to saturate all the available binding sites on the bead. The oligo sequence used was 5'-[BiotinTEG]TTT TTT ACT GGC CGT CGT TTT ACA-3' The six T's closest to the 5'end were inserted to form a linker for the 18-mer oligo. These may not be necessary.

The beads were then captured (magnetically) and excess oligo removed by washing three times with the same 1M buffer and resuspended into 100 ul (corresponding to a 10-fold diluted bead density compared to the original stock). A 40 ul batch of beads was incubated for 20 minutes at 45° C. with complementary oligo labeled with Cy3 dye (at a concentration of 1 µM). The sequence of the oligo is 5'-Cy3-TGT AAA ACG ACG GCC AGT-3'. Again, 1M NaCl conditions were used. The beads were then washed thrice to remove excess labeled oligo and resuspended in 1×TE with 0.001% TWEEN. The sample was arrayed as described in Example 2, on a magnetic chip with islands at a spacing of 20 µm in each direction.

A confocal fluorescence scan of the chip was performed at 488 nm excitation (using an argon laser) and signal collected at 570 nm. FIG. 13 shows a fluorescence image of a 30×30 array obtained from this experiment. The image was obtained using a 50× objective with a photomultiplier tube at low setting with a 570 nm centered optical bandpass filter. The scale of the image is 5 µm/count; thus the size of the array is approximately 0.6 mm on each side. The white pixels represent beads bearing oligos (probes) to which complementary Cy3-labeled oligos are bound. Varying levels of intensity indicate that different numbers of Cy3-labeled oligos bound to different beads. (White pixels indicate a greater number of bound oligos.) The figure shows trapping of zero, one, or multiple beads at various locations. Bead clumping and trapping of multiple beads at the edges of the array can be reduced by using a field-circulator loop.

Example 4

Performing Genotyping Using a Random Array of Magnetic Beads

A genotyping assay is performed in a fashion essentially identical to that described in Fan, J., et al., referenced above, except that rather than employing a substrate-bound oligonucleotide array, the magnetic bead array of the present invention is used. A pool of magnetic beads is encoded with unique complementary tags as described, and hybridization to the labeled sample is performed. Following off-chip hybridization, the magnetic beads are dispensed onto the magnetic chip as described above and detected using either confocal laser scanning or a charge coupled device. Such a reformatting approach allows use of a populations of beads that have been tagged in advance, and thus provides an efficient and flexible means of utilizing the random order array of magnetic beads for genotyping and other applications.

We claim:

1. A device for forming an array of magnetic particles, the device comprising: a substrate comprising a plurality of magnetic regions having gaps between them, wherein the substrate comprises a surface, wherein the magnetic regions have a maximum length parallel to the surface of the substrate and a maximum width parallel to the surface of the substrate with the maximum length being greater than the maximum width, and wherein the magnetic regions produce a plurality of localized magnetic fields when magnetized, and wherein adjacent magnetic regions are so aligned with one another in the directions of their maximum length that the localized magnetic fields are sufficient to trap a magnetic particle between adjacent magnetic regions with a trapping energy at least three times greater than the thermal energy of the particle at room temperature and the gaps are available for fluid flow among them and are also available for occupancy by magnetic particles prior to introduction of magnetic particles to the device so that forces generated by the localized magnetic fields between adjacent regions can trap magnetic particles in the gaps between them, wherein the magnetic regions project above the surface of the substrate, and wherein the magnetic regions comprise a layer of magnetic material and a layer of nonmagnetic material, wherein the layer of nonmagnetic material is located between the substrate and the layer of magnetic material.

2. The device of claim 1, wherein the localized magnetic fields are sufficient to trap a magnetic particle with a trapping energy at least an order of magnitude greater than the thermal energy of the particle at room temperature.

3. The device of claim 1, wherein the magnetic material regions are arranged in a pattern of mutually perpendicular rows and columns.

4. The device of claim 1, wherein the magnetic regions are arranged in an array of subarrays configuration.

5. The device of claim 1, wherein the magnetic regions are substantially uniform in shape.

6. The device of claim 1, wherein the magnetic regions are substantially rectangular in shape.

7. The device of claim 1, wherein the magnetic regions are substantially uniform in size.

8. The device of claim 1, wherein the number of magnetic regions is at least 1000 per centimeter squared.

9. The device of claim 1, wherein the number of magnetic regions is at least 10,000 per centimeter squared.

10. The device of claim 1, wherein the number of magnetic regions is at least 100,000 per centimeter squared.

11. The device of claim 1, wherein the number of magnetic regions is at least 250,000 per centimeter squared.

12. The device of claim 1, wherein the number of magnetic regions is at least 1,000,000 per centimeter squared.

13. The device of claim 1, wherein adjacent magnetic regions are separated by a gap approximately equal in size to the size of a magnetic particle having a largest dimension of less than approximately 200 µm.

14. The device of claim 13, wherein the magnetic particle has a greatest dimension selected from the group consisting of: 30 nm, 100 nm, 300 nm, 500 nm, 1 µm, 3 µm, 5 µm, and 10 µm.

15. The device of claim 14 wherein the magnetic particle is substantially spherical, and the greatest dimension of the particle is the diameter of the particle.

16. The device of claim 13, wherein the gap has a minimum length of approximately 1 micron.

17. The device of claim 13, wherein the gap has a minimum length of approximately 3 microns.

18. The device of claim 13, wherein the gap has a minimum length of approximately 5 microns.

19. The device of claim 1, wherein adjacent magnetic regions are separated by a gap having a greatest dimension approximately equal in size to the greatest dimension of a magnetic particle.

20. The device of claim 19, wherein the gap has a greatest dimension approximately equal in size to the greatest dimension of a magnetic particle having a greatest dimension selected from the group consisting of: 30 nm, 100 nm, 300 nm, 500 nm, 1 µm, 3 µm, 5 µm, and 10 µm.

21. The device of claim 20, wherein the magnetic particle is substantially spherical, and the greatest dimension of the particle is the diameter of the particle.

22. The device of claim 1, wherein the magnetic regions comprise a magnetic material.

23. The device of claim 22, wherein the magnetic material is a ferromagnetic material.

24. The device of claim 1, wherein the substrate comprises a nonmagnetic material.

25. The device of claim 24, wherein the magnetic regions are surrounded by nonmagnetic material.

26. The device of claim 1, wherein the magnetic regions comprise cobalt.

27. The device of claim 1, wherein the magnetic regions are formed using photolithography.

28. The device of claim 1, wherein the magnetic particles are magnetic beads.

29. The device of claim 1, wherein the magnetic particles are paramagnetic particles.

30. The device of claim 1, wherein the magnetic particles are superparamagnetic particles.

31. The device of claim 1, further comprising a magnet for magnetizing and demagnetizing the magnetic regions.

32. The device of claim 1, wherein the size, shape, and spacing of the regions are selected to increase the likelihood of trapping only a single magnetic particle within the gaps.

33. The device of claim 1, wherein the distance between the ends of adjacent magnetic regions in the dimension of the maximum length is 200 microns or less.

34. A device for forming an array of magnetic particles, the device comprising: a substrate comprising a plurality of magnetic regions having gaps between them, wherein the substrate comprises a surface, and wherein the magnetic regions produce a plurality of localized magnetic fields when magnetized, wherein the magnetic regions have a maximum length parallel to the surface of the substrate and a maximum width parallel to the surface of the substrate, and wherein a plurality of regions are spaced apart along the dimension of the maximum length and a plurality of regions are spaced apart along the dimension of the maximum width, so that the distance separating adjacent regions in the dimension of the maximum length is less than the distance separating adjacent regions in the dimension of the maximum width, and, wherein the localized magnetic fields are sufficient to trap a magnetic particle with a trapping energy at least three times greater than the thermal energy of the particle at room temperature, wherein the magnetic regions project above the surface of the substrate, and wherein the magnetic regions comprise a layer of magnetic material and a layer of nonmagnetic material, wherein the layer of nonmagnetic material is located between the substrate and the layer of magnetic material.

35. A device for forming an array of magnetic particles, the device having an upper surface and comprising: a substrate comprising a plurality of magnetic regions having gaps between them, wherein the magnetic regions have north and south poles that produce a plurality of localized magnetic fields when magnetized, wherein adjacent magnetic regions have ends with opposite magnetic polarities facing each other across a gap between them, wherein the magnetic regions are appropriately shaped and have an appropriate size so as to generate localized magnetic fields that exist substantially in a volume between adjacent north and south poles of adjacent magnetic regions above and parallel to the upper surface of the device and wherein the magnetic fields are sufficient to trap a magnetic particle with a trapping energy at least three times greater than the thermal energy of the particle at room temperature and the gaps are available for fluid flow among them and are also available for occupancy by magnetic particles prior to introduction of magnetic particles to the device so that forces generated by the localized magnetic fields between adjacent regions can trap magnetic particles in the gaps between them, wherein the magnetic regions project above the surface of the substrate, and wherein the magnetic regions comprise a layer of magnetic material and a layer of nonmagnetic material, wherein the layer of nonmagnetic material is located between the substrate and the layer of magnetic material.

36. The device of any of claims 1, 2, 34, or 35, wherein the thermal energy of the particle is approximately 0.025 eV.

37. The device of any of claims 1, 2, 34, or 35, wherein the magnetic regions have walls that are substantially perpendicular to the substrate.

38. A device for forming an array of magnetic particles, the device comprising: a substrate comprising a plurality of magnetic regions having gaps between them, wherein the substrate comprises a surface, wherein the magnetic regions have a maximum length parallel to the surface of the substrate and a maximum width parallel to the surface of the substrate with the maximum length being greater than the maximum width, and wherein the magnetic regions produce a plurality of localized magnetic fields when magnetized, and wherein adjacent magnetic regions are so aligned with one another in the directions of their maximum length that the localized magnetic fields are sufficient to trap a magnetic particle between adjacent magnetic regions with a trapping energy at least three times greater than the thermal energy of the particle at room temperature and the gaps are available for fluid flow among them and are also available for occupancy by magnetic particles prior to introduction of magnetic particles to the device so that forces generated by the localized magnetic fields between adjacent regions can trap magnetic particles in the gaps between them, wherein at least a portion of the device comprises a biocompatible material.

39. The device of claim 38, wherein at least the surface of the substrate and the magnetic regions comprises a biocompatible material.

40. A device for forming an array of magnetic particles, the device comprising: a substrate comprising a plurality of magnetic regions having gaps between them, wherein the substrate comprises a surface, wherein the magnetic regions have a maximum length parallel to the surface of the substrate and a maximum width parallel to the surface of the substrate with the maximum length being greater than the maximum width, and wherein the magnetic regions produce a plurality of localized magnetic fields when magnetized, and wherein adjacent magnetic regions are so aligned with one another in the directions of their maximum length that the localized magnetic fields are sufficient to trap a magnetic particle between adjacent magnetic regions with a trapping energy at least three times greater than the thermal energy of the particle at room temperature and the gaps are available for fluid flow among them and are also available for occupancy by magnetic particles prior to introduction of magnetic particles to the device so that forces generated by the localized magnetic fields between adjacent regions can trap magnetic particles in the gaps between them, wherein the magnetic regions project above the surface of the substrate, and wherein the magnetic regions comprise a layer of magnetic material and a layer of nonmagnetic material, wherein the layer of nonmagnetic material is located between the substrate and the layer of magnetic material, wherein the substrate comprises silicon.

41. A device for forming an array of magnetic particles, the device comprising: a substrate comprising a plurality of magnetic regions having gaps between them, wherein the substrate comprises a surface, wherein the magnetic regions have a maximum length parallel to the surface of the substrate and a maximum width parallel to the surface of the substrate with the maximum length being greater than the maximum width, and wherein the magnetic regions produce a plurality of localized magnetic fields when magnetized, and wherein adjacent magnetic regions are so aligned with one another in the directions of their maximum length that the localized magnetic fields are sufficient to trap a magnetic particle between adjacent magnetic regions with a trapping energy at least three times greater than the thermal energy of the particle at room temperature and the gaps are available for fluid flow among them and are also available for occupancy by magnetic particles prior to introduction of magnetic particles to the device so that forces generated by the localized magnetic fields between adjacent regions can trap magnetic particles in the gaps between them, further comprising a flux circulator disposed around the magnetic regions.

42. A device for forming an array of magnetic particles, the device comprising: a substrate comprising a plurality of magnetic regions having gaps between them, wherein the substrate comprises a surface, wherein the magnetic regions have a maximum length parallel to the surface of the substrate and a maximum width parallel to the surface of the substrate with the maximum length being greater than the maximum width, and wherein the magnetic regions produce a plurality of localized magnetic fields when magnetized, and wherein adjacent magnetic regions are so aligned with one another in the directions of their maximum length that the localized magnetic fields are sufficient to trap a magnetic particle between adjacent magnetic regions with a trapping energy at least three times greater than the thermal energy of the particle at room temperature and the gaps are available for fluid flow among them and are also available for occupancy by magnetic particles prior to introduction of magnetic particles to the device so that forces generated by the localized magnetic fields between adjacent regions can trap magnetic particles in the gaps between them, farther comprising a plurality of photodetectors located in proximity to locations for trapping the magnetic particles so as to detect an optical signal from trapped particles.

43. A device for forming an array of magnetic particles, the device comprising: a substrate comprising a plurality of magnetic regions having gaps between them, wherein the substrate comprises a surface, wherein the magnetic regions have a maximum length parallel to the surface of the substrate and a maximum width parallel to the surface of the substrate with the maximum length being greater than the maximum width, and wherein the magnetic regions produce a plurality of localized magnetic fields when magnetized, and wherein adjacent magnetic regions are so aligned with one another in the directions of their maximum length that the localized magnetic fields are sufficient to trap a magnetic particle between adjacent magnetic regions with a trapping energy at least three times greater than the thermal energy of the particle at room temperature and the gaps are available for fluid flow among them and are also available for occupancy by magnetic particles prior to introduction of magnetic particles to the device so that forces generated by the localized magnetic fields between adjacent regions can trap magnetic particles in the gaps between them, farther comprising a microfluidic assembly, wherein the microfluidic assembly comprises channels positioned in communication with the magnetic regions so as to allow introduction of fluids to the magnetic regions via the channels so that the fluids contact the magnetic regions following introduction of the fluids via the channels.

44. A device for forming an array of magnetic particles, the device comprising: a substrate comprising a plurality of magnetic regions having gaps between them, wherein the substrate comprises a surface, wherein the magnetic regions have a maximum length parallel to the surface of the substrate and a maximum width parallel to the surface of the substrate with the maximum length being greater than the maximum width, and wherein the magnetic regions produce a plurality of localized magnetic fields when magnetized, and wherein adjacent magnetic regions are so aligned with one another in the directions of their maximum length that the localized magnetic fields are sufficient to trap a magnetic particle between adjacent magnetic regions with a trapping energy at least three times greater than the thermal energy of the particle at room temperature and the gaps are available for fluid flow among them and are also available for occupancy by magnetic particles prior to introduction of magnetic particles to the device so that forces generated by the localized magnetic fields between adjacent regions can trap magnetic particles in the gaps between them, wherein the magnetic regions project above the surface of the substrate, and wherein the magnetic regions comprise a layer of magnetic material and a layer of nonmagnetic material, wherein the layer of nonmagnetic material is located between the substrate and the layer of magnetic material, further comprising a plurality of magnetic particles.

45. The device of claim 44, wherein the magnetic particles are substantially uniform in size and shape and are magnetic beads.

46. The device of claim 44, wherein the magnetic particles are substantially uniform in size and shape and are paramagnetic beads.

47. The device of claim 44, wherein the magnetic particles are substantially uniform in size and shape and are superparamagnetic beads.

48. The device of claim 44, wherein the magnetic particles are trapped by the localized magnetic fields.

49. The device of claim 44, wherein each of a plurality of the magnetic particles comprises a detectable moiety.

50. The device of claim 49, wherein the detectable moiety comprises a fluorescent or luminescent molecule.

51. The device of claim 49, wherein the detectable moiety comprises a nucleic acid.

52. The device of claim 51, wherein the nucleic acid comprises a hybridization tag.

53. The device of claim 44, wherein each of a plurality of the magnetic particles has a probe attached thereto.

54. The device of claim 53, wherein the probe comprises a binding ligand.

55. The device of claim 53, wherein the probe comprises a nucleic acid molecule.

56. The device of claim 53, wherein the probe comprises a protein.

57. A device for forming an array of magnetic particles, the device comprising:
a substrate comprising a plurality of magnetic regions, wherein the substrate comprises a surface, and wherein the localized magnetic regions produce a plurality of localized magnetic fields concentrated in gaps between the regions, and wherein the magnetic regions project above the surface of the substrate and have a maximum length parallel to the surface of the substrate and a maximum width parallel to the surface of the substrate, with the maximum length being greater than the maximum width, wherein a plurality of regions are spaced apart along the dimension of the maximum length and a plurality of regions are spaced apart along the dimension of the maximum width, and wherein the distance separating adjacent regions in the dimension of the length is less than the distance separating adjacent regions in the dimension of the width, further comprising a plurality of magnetic particles wherein the magnetic regions project above the surface of the substrate, and wherein the magnetic regions comprise a layer of magnetic material and a layer of nonmagnetic material, wherein the layer of nonmagnetic material is located between the substrate and the layer of magnetic material.

58. The device of claim 57, wherein the magnetic regions are substantially uniform in size and shape.

59. The device of claim 57, wherein the magnetic regions are arranged in a pattern of mutually perpendicular rows and columns.

60. The device of claim 57, comprising:
a nonmagnetic substrate; and
a plurality of magnetic regions located on the substrate, wherein a localized magnetic field exists between adjacent magnetic material regions when magnetized.

61. The device of claim 60, further comprising a plurality of magnetic particles.

62. The device of claim 60, wherein the magnetic regions are substantially uniform in size and shape.

63. The device of claim 60, wherein the magnetic regions are arranged in a pattern of mutually perpendicular rows and columns.

64. The device of claim 60, wherein the magnetic regions project above the surface of the substrate.

65. The device of claim 1, 34, or 57, wherein the magnetic regions have a maximum length that is between 3 and 5 times as great as the maximum width or between 5 and 10 times as great as the maximum width.

66. The device of claim 1, 34, or 57, wherein adjacent magnetic regions are separated by a gap of between 1 and 5 microns or between 5 and 15 microns.

67. The device of claim 1, 34, or 57, wherein the magnetic regions are not rectangular.

* * * * *

UNITED STATES PATENT AND TRADEMARK OFFICE
CERTIFICATE OF CORRECTION

| | | |
|---|---|---|
| PATENT NO. | : 7,682,837 B2 | Page 1 of 1 |
| APPLICATION NO. | : 09/923752 | |
| DATED | : March 23, 2010 | |
| INVENTOR(S) | : Jain et al. | |

It is certified that error appears in the above-identified patent and that said Letters Patent is hereby corrected as shown below:

In the Specification Under Column 1:

• Please replace Column 1, line no. 14-17 with:

-- FEDERALLY-SPONSORED RESEARCH OR DEVELOPMENT
This invention was made with Government support under contract HG000205 awarded by the National Institutes of Health. The Government has certain rights in this invention. --

Signed and Sealed this
Twentieth Day of March, 2012

David J. Kappos
*Director of the United States Patent and Trademark Office*